US008022235B2

(12) United States Patent
Pinchuk et al.

(10) Patent No.: US 8,022,235 B2
(45) Date of Patent: Sep. 20, 2011

(54) COMPOSITIONS OF PHOSPHOLIPID ETHER BORONIC ACIDS AND ESTERS AND METHODS FOR THEIR SYNTHESIS AND USE

(75) Inventors: Anatoly Pinchuk, Madison, WI (US); Jamey P. Weichert, Fitchburg, WI (US); Marc Longino, Verona, WI (US)

(73) Assignee: Cellectar, Inc., Madison, WI (US)

( * ) Notice: Subject to any disclaimer, the term of this patent is extended or adjusted under 35 U.S.C. 154(b) by 443 days.

(21) Appl. No.: 12/156,258

(22) Filed: May 30, 2008

(65) Prior Publication Data

US 2009/0018357 A1    Jan. 15, 2009

Related U.S. Application Data

(60) Provisional application No. 60/932,749, filed on Jun. 1, 2007.

(51) Int. Cl.
*C07F 11/00* (2006.01)
*C07F 7/02* (2006.01)
(52) U.S. Cl. .......................... 554/77; 514/64
(58) Field of Classification Search ............... 554/77; 514/64
See application file for complete search history.

(56) References Cited

U.S. PATENT DOCUMENTS

| 4,925,649 | A | 5/1990 | Counsell |
| 4,965,391 | A | 10/1990 | Counsell |
| 5,087,721 | A | 2/1992 | Counsell |
| 5,347,030 | A | 9/1994 | Counsell |
| 5,369,097 | A | 11/1994 | Salari |
| 5,795,561 | A | 8/1998 | Counsell |
| 6,417,384 | B1 | 7/2002 | Counsell |
| 6,939,985 | B1 * | 9/2005 | Marcuccio et al. ............ 558/288 |
| 2002/0065429 | A1 | 5/2002 | Counsell |
| 2007/0020178 | A1 * | 1/2007 | Weichert et al. ............. 424/1.11 |

FOREIGN PATENT DOCUMENTS

| WO | 2005/063774 A1 | 7/2005 |
| WO | WO 2005063774 A1 * | 7/2005 |
| WO | WO 2005/084716 A2 | 9/2005 |

OTHER PUBLICATIONS

Kabalka et al. Synthesis of radioiodInated aryl iodides via boronate precursors. Nucl. Med. Biol., 2002, vol. 29(8), pp. 841-843, Abstract only.*
International Search Report for corresponding PCT Application No. PCT/US2008/006842 dated Sep. 2, 2008.
Kabalka et al., Synthesis of radioiodinated aryl iodides via boronate precursors, Nucl. Med. Biol., 2002, vol. 29(8), pp. 841-843, Abstract only.
Arthur, G. et al., The Inhibition of Cell Signaling Pathways . . . R. Biochim Biophys Acta. (1998) 1390:85-102.

(Continued)

*Primary Examiner* — Deborah D Carr
(74) *Attorney, Agent, or Firm* — Wolf, Greenfield & Sacks, P.C.

(57) ABSTRACT

The present invention discloses boronic acids and esters of phospholipid ether analogs and methods for their synthesis and use. The boronic acids and esters of phospholipid ether analogs described herein can be used in treating cancer and in particular can be used in conjunction with radiation therapy, such as external beam radiation therapy and neutron capture therapy to specifically target and kill cancer cells.

14 Claims, 7 Drawing Sheets

NM294

NM324

NM404

NM412

OTHER PUBLICATIONS

Becher, R. et al., Phase II Trial of Orally Administered Miltefosine . . . Onkologie-Germany (1993) 16; 1:11-15.

Berdel, W.E. et al., Daily Oral Miltefosine (Hexadecylphosphocholine) . . . Onkologie-Germany (1992) 15:238-242.

Clezy, P.S. et al., The Chemistry of Pyrrolic Compounds, Aust. J.Chem., (1969) 22:239-49.

Counsell, R.E. et al., Tumor Visualization With a Radioiodinated Phospholipid . . . (1990) 31; 3:332-336.

Counsell, R.E. et al, Synthesis and Evluation of Radioiodinated Phospholipd Ether . . . Quart J. Nucl Med. (1997) 41(suppl 1):14-16.

Curley, SA et al., Radiofrequency Ablation of Unresectable Primary and Metastitic . . . Ann Surg. (1999) 230:1-8.

De Gramont, A. et al., Randomized Trial Comparing Monthly Low-Dose Leucovorin and . . . J. Clin. Oncol. (1997) 15:808-815.

Fong, Y. et al., Clinical Score for Predicting Recurrence After Hepatic Resection . . . Ann Surg. (1999) 230:309-318.

Giacchetti, S. et al., Phase III Multicenter Randomized Trial of Oxaliplatin Added . . . J. Clin. Oncol. (2000) 18:136-147.

Goud, T.V. et al., Synthesis of 8-Heteroatom-Substituted 4,4-Difluoro-4-Bora-3A, 4A-Diaza-S-Indacene Dyes (BODIPY), Tetrahedron 62 (2006) 5084-5091.

Greven, K. et al., Can Positron Emission Tomography Distinguish Tumor . . . Cancer Journal Scientifica American (1997) 3:353-357.

Ike, H. et al., Results of Agressive Resection of Lung Matastases From Colorectal Carcinoma . . . Dis colon Rectum (2002) 45:468-473.

Imboden, M. et al., The Level of MHC Class I Expression on Murine Adenocarcinoma Can Change . . . Cancer Res. (2001) 61:1500-1507.

Kallman, R. F. Rodent Tumor Models in Experimental Cancer Therapy Pergamon Press, New York, (1987) pp. 111-132.

Lencioni, R. et al., Percutaneous Radiofrequency Thermal Ablation of Liver Malignancies: Techniques . . . Abdom Imaging (2001) 26:345-360.

Liebeskind L.S. et al., Heteroaromatic Thioether—Bornic Acid Cross-Coupling . . . Dept. of Chem., Emory University, Organic Letters (2002) 4; 6:979-981.

Longino, M.A. et al., Tumor Selective Rentention of NM404—Involvement of Phospholipase D. Molecular Imaging (2004), 3(3).

Maier, O. et al., Fluorescent Lipid Probes: Some Properties and Application (A Review) Chemistry and Physics of Lipids 116 (2002) 3-18.

Mayr, N.A. et al., Method and Timing of Tumor Volume Measurement for Outcome . . . Int. J. of Rad., Oncol., Bio., Phys. (2002) 52; 1:14-22.

Meta-Analysis:Modulation of Fluorouracil by . . . Advanced Colorectal Cancer Meta-Analysis Project. J. clin. Oncol. (1992) 10:896-903.

Moser, A.R. et al., Specificity of NM404 for Hyperplasia Versus Neoplasia in the . . . Online Aug. 15-18, 2003 Presentation No. 305.

O'Dwyer, P.J. et al., Follow-Up of Stage B and C Colorectal Cancer in the United States and . . . Seminars in Onology (2001) 28:Suppl-9.

Penna, C., et al., Colorectal Metastasis (Liver and Lung), Surg. clin. North Amer. (2002) 82:1075-10xi.

Pickhardt, P.J. et al., Computed Tomographic Virtual Colonoscopy to Screen for Colorectal . . . NE J. Med. (2003) 349; 23:2191-2200.

Plotzke, K.P. et. al., Selective Localization of a Radioiodinated Phospholipid Ether Analog in Human Tumor . . . J. Nucl. Med. (1993) 34(5):787-792.

Plotzke, K.P. et al., Selective Localization of Radioiodinated Alkylphosphocholine . . . Int, J. RadPart B, Nucl. Med. & Biology. (1992) 19(7):765-773.

Rampy, M.A. et al., Biological Disposition and Imaging of a Radioiodinated Alkylphosphocholine in Two Rodent . . . J. Nucl. Med. (1996) 37(9):1540-1545.

Rampy, M.A. et al., Synthesis and Biological Evaluation of Radioiodinated Phospholipid Ether Stereoisomers, J. Med. Chem. (1995) 38:3156-3162.

Saltz, L.B. et al., Irinotecan Plus Fluorouracil and Leucovorin for Metastiatic Colorectal Cancer . . . , N. Engl. J. Med. (2000) 343:905-91.

Snyder, F. et al., Alkyl and Alk-1-Enyl Ethers of Glycerol in Lipids From Normal and Neoplastic Human Tissues, Cancer Research. (1969) 29:251-257.

Snyder, F, et al., Occurrence and Nature of O-Alkyl and O-Alkyl-L-Enyl Moieties of Glycerol in Lipids of Morris . . . Biochem Biophys Acta. (1969) 176:502-510.

Solbiati, L. et al., Percutaneous Radio-Frequency Ablation of Hepatic Metastases From Colorectal Cancer: Long-Term . . . Radiology (2001) 221:159-166.

Stahl, A. et al., PET/CT Molecular Imaging in Abdominal Oncology, Abdominal Imaging (2004) 29:3(388-397).

Terwogt, J.M.M. et al., Phase II Trial of Topically Applied Miltefosine Solution in Optients With Skin-Metastasized . . . British J. of Cancer (1999) 79:1158-1161.

Wagner, R. et al., Boron-Dipyrromethene Dyes for Incorporation in Synthetic Multi-Pigment Light-Harvesting Arrays, Pure & Appl. Chem., (1996) 68 7:1373-1380.

Wang, H.E. et al., Molecular Imaging With 123I-FIAU, 18F-FUdR, 18F-FET, and 18F-FDG For Monitoring Herpes . . . J. of Nuclear Med. (Jul. 2006) 47; 7:1161-1171.

Weber, S.M. et al., Interleukin-1 Gene Transfer Results in CD8-Dependent Regression of Murine CT26 Liver Tumors, Ann. Surg. Oncol. (1999) 6:186-194.

Weichert, J.P. et al., Initial Clinical Imagining Results With NM404 in Non-Small Cell Lung Cancer, Molecular Imaging Online (2004) 3; 3:269-270.

Wichmann, M.W. et al., The Colorectal Cancer Study Group. Carcinoembryonic Antigen for the Detection . . . Anticancer Research (2000) 20:4953-4955.

Zasadny, K.R. et al., Predicted Dosimetry for I-131-NM404, A Phospholipid Ether Agent for Tumor Imaging and Possible Therapy, J Nucl Med. (1999) 40(5):39P.

Quon, A. et al., "Flying Through" and "Flying Around" A PET/CT Scan: Pilot Study . . . J. of Nuclear Med. (Jul. 2006) 47; 7:1081-1087.

Sik, M.D. et al., Neoplastic Transformation and Tumorrigensis Associated With Overexpress . . . Database Biosis(Online) (Oct. 2001) XP002365147 Database No. PREV200100523916.

Hirokazu O. et al., Increased Activity and Expression of Phospholipase D2 in Human . . . Database Biosis (Online) (2003) XP002365146 Database No. PREV00300566956.

Dong-Young, N. et al., Overexpression of Phospholipase D1 in Human Breast Cancer Tissues, Database Biosis (Online) (Dec. 2000) XP002365186 Database No. PREV200100047408.

Weichert, J. et al., Specificity of NM404 for Hyperplasia versus Neoplasia in the APC . . . Oasis—Online Abstrct Submission and Invitation System, 1996-2007.

Weichert JP et al "Evaluation of 125I-NM404 in a Spontaneous Murine Pancreatic Adenocarcinoma . . . ", Aug. 2003, 2nd Annual Meeting of the Society of Molecular Imaging, San.

Weichert J. et al., Radioiodination Via Isotope Exchange in Pivalic Acid, Appl. Radiat Isot (1986) vol. 37, No. 8, 907-913.

Weichert J. et al., Polyiodinated Triglyceride Analogs As Potential Computed Tomography Imaging Agents for the Liver, J Med Chem (1995) 38, 636-646.

Pinchuk A. et al., Synthesis and Structure-Activity Relationship Effects on the Tumor Avidity of Radioiodinated Phospholipid Ether Analogues, J Med Chem (2006), 49, 2155-2165.

* cited by examiner

COMPOSITIONS OF PHOSPHOLIPID ETHER BORONIC ACIDS AND ESTERS AND METHODS FOR THEIR SYNTHESIS AND USE

RELATED APPLICATIONS

This application claims the benefit of priority to U.S. Provisional Patent Application Ser. No. 60/932,749, filed Jun. 1, 2007, entitled "Compositions of Phospholipid Ether Boronic Acids and Esters and Methods for Their Synthesis and Use," by Pinchuk et al.

FIELD OF THE INVENTION

The current invention is directed to boronic acids and esters of phospholipid ether (PLE) analogs and methods for their synthesis and use. The PLE boronic acids and esters disclosed herein can be used to specifically target cancer cells and can be used in external beam radiation and neutron capture therapy to treat cancer patients.

BACKGROUND OF THE INVENTION

Cancer is a class of diseases characterized by the uncontrolled division of the affected cells and the ability of these cells to spread, either by invasion, the direct growth of the cancer or neoplastic cells into unaffected tissue or by metastatic growth, the implantation of metastatic cells into distant sites. While there are various therapies and pharmaceuticals developed to treat cancer, the variability of the disease, from tissue to tissue and its ability to develop metastatic growths in distant location together with its resistance to drugs and therapies has resulted in an enormous amount of research to identify therapies or drugs that are effective in a wide variety of cancers and that are non-toxic or at least non-fatal to healthy cells.

Phospholipids are the major lipid component of cell membranes. Ether phospholipids are a minor phospholipid subclass differing by having an ether linkage at the C-1 carbon of the glycerol backbone rather than the normal ester bond. Alkyl phosphocholines (APC), for example, hexadecylphosphocholine (HPC), are another subclass of compounds that have shown antineoplastic targeting activity. Assessment of this new class of PLE analogs as cancer treatments in several animal tumor models provided by the inventors revealed that NM404 (18-[4-Iodophenyl]-octadecyl phosphocholine) and similar PLE and APC analogs, specifically accumulate and are selectively retained in primary and/or metastatic tumors. While some compounds such as, fluorodeoxyglucose (FDG) are commonly used in imaging applications for its high uptake in cancer tissues, FDG also accumulates in inflammatory and granulomatous lesions thereby giving false positives, does not accumulate in bone metastases of prostate cancer and further, is rapidly cleared in the urine thereby resulting in a short time frame for use and also in high background in the kidneys and bladder. Further, FDG also has no therapeutic potential and its clinical use is solely as a means of imaging it incorporation into high metabolic tissues. Thus, FDG can not begin to approach the specificity and versatility of PLE and APC analogs.

Further investigation of radioiodinated PLE and APC analogs, such as radioiodinated NM404 has demonstrated, in 37 of 37 models investigated, a remarkable tumor selectivity of these compounds in a wide variety of tumor models. See, for example, U.S. patent application Ser. Nos. 10/906,687, 11/177,740, 11/316,620 and 11/382,645. Due to deficiencies in metabolic phospholipase enzymes in the membranes of malignant tumor cells, the prevailing hypothesis for this specificity is that phospholipid ether analogs become trapped exclusively in tumor cell membranes because of their inability to become metabolized and eliminated by the cancerous cell. Thus, the differential clearance rates of phospholipid ethers from normal cells versus neoplastic tumor cells are responsible for this specificity. Results obtained in a variety tumor models indicate that PLE and APC analogs, such as, NM404 are sequestered and selectively retained by viable tumor cells and localize in both primary and metastatic lesions regardless of anatomic location including those found in lymph nodes.

One recognized treatment for cancer is radiotherapy which uses ionizing radiation to kill cancer cells. Such treatments can be given in a variety of ways, such as X-rays, gamma rays, neutron beams or implanted particles. While radiation therapy is used in over half of all cancer patients it is limited by its inability to specifically and precisely target cancer cells and thereby limit its toxicity to healthy tissue. In an effort to limit radiation administered to healthy tissues during treatment by external radiation, methods for internal radiation treatment are being developed. For example, endocavitary radiation therapy (Endo RT) and endo-luminal RT can be performed on select individual and is preformed by the insertion of a contact X-ray tube into a tumor or into tubular structures such as the bronchi or esophagus to limit the deleterious effect of radiation on healthy cells. However, with both external radiation and with endo radiation therapy the radiation dose is delivered non-specifically to the region proximate to the tumor but not delivered specifically or selectively to the metastatic cells. Further, in an effort to solve the problem of non-specific radiation, radioimmunotherapy—radioactive antibodies—have been developed that are specific for epitopes displayed by neoplastic cells. However, while antibodies have exquisite specificity, their specificity is directed to only to a single cognate epitope which is specific for each neoplastic cell type. Thus, neither of the methods described above are adequate for the systemic administration of cancer therapies specifically directed to neoplastic cells.

Boron neutron capture therapy (BNCT) is a binary radiation therapy having two components each of which, independently, has only minor effects on cells. BNCT utilizes the neutron capture by which a neutron collides with an atomic nucleus, boron, to produce alpha particles, lithium nuclei and ionizing radiation. Both the alpha particle and the lithium ion produce closely spaced ionizations in the vicinity of the reaction, approximately 10 μm, or the diameter of a cell. Therefore, the ability to target and sequester the boron atom in the cancer cell would allow the products of the neutron bombardment to specifically irradiate cancer cells.

External beam radiation therapy is similar to BNCT in that linear accelerators are used to produce a beam of electrons that can be focused to hit a desired target. When the target is an appropriate alloy (such as $^{10}B$), collision results in the liberation of gamma radiation. Gamma rays are characterized by a short wavelength and high energy. Due to their high energy, the liberated gamma rays provide lethal radiation only to adjacent tissue.

Currently, one limitation of BNCT and external beam radiation is the ability to specifically target cancer cells and limit the deleterious effects of the radiation in surrounding healthy tissue.

SUMMARY OF THE INVENTION

The present invention discloses boronic esters of phospholipid ether analogs and methods for their synthesis and use.

The boronic esters of the phospholipid ether analogs described herein can be used in treating cancer and in particular can be used in conjunction with radiation therapy, such as external beam radiation therapy and neutron capture therapy to specifically target cancer cells.

Accordingly, in one exemplary embodiment, the invention includes boronic acids or esters of a phospholipid ether analog having the structure:

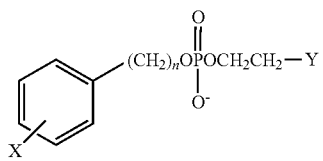

wherein X is selected from the group consisting of

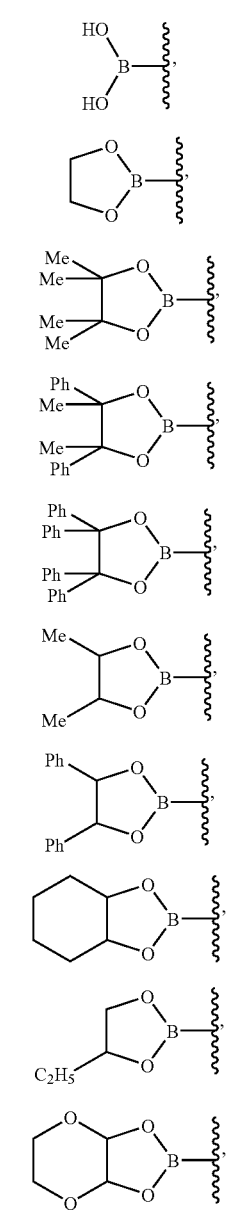

-continued

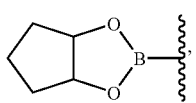 56

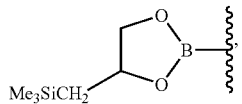 57

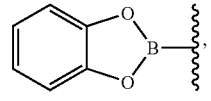 58

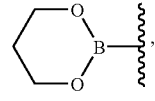 59

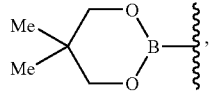 60

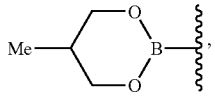 61

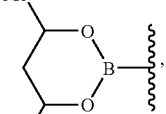 62

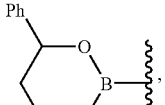 63

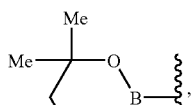 64

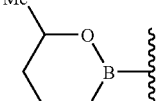 65

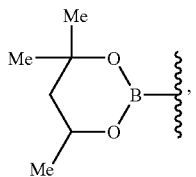 66

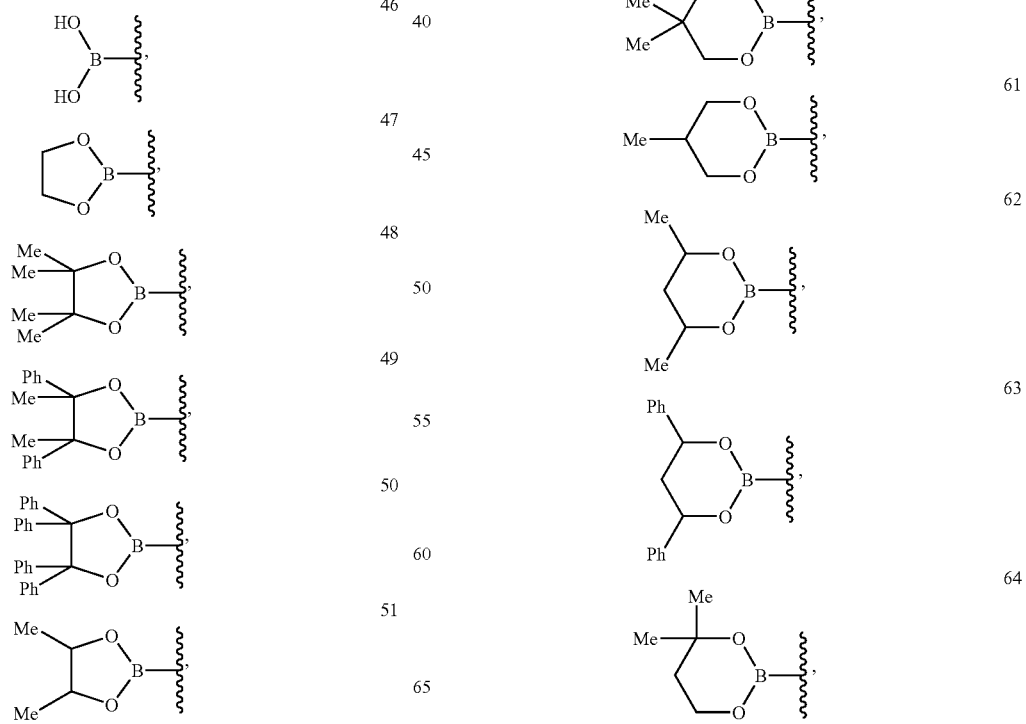
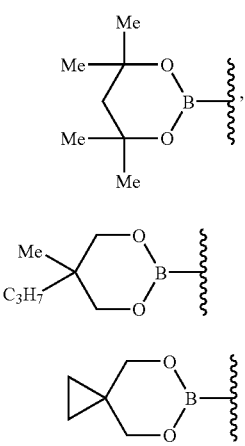
wherein n is an integer between 8 and 30; and Y is selected from the group comprising NH$_2$, NHR, NR$_2$, and NR$_3$, wherein R is an alkyl or arylalkyl substituent.
In some preferred embodiments, the boronic acid or ester of the phospholipid ether analog has the formula:
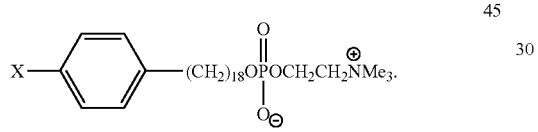
In these embodiments, X is selected from the group consisting of:

In yet another exemplary embodiment, the invention includes a boronic ester of a phospholipid ether analog having the structure wherein X is selected from the group consisting of:

-continued

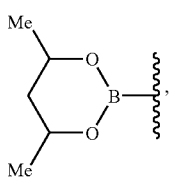
62

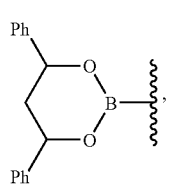
63

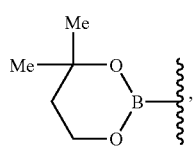
64

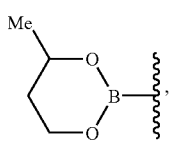
65

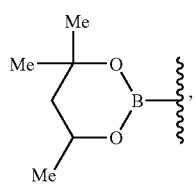
66

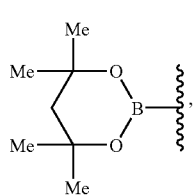
67

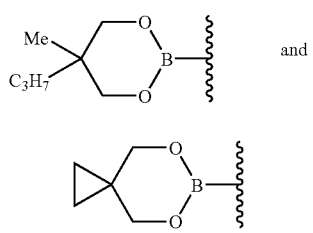
68 and

69 wherein n is an integer between 8 and 30; and Y is selected from the group consisting of H, OH, OCH$_3$, OC$_2$H$_5$, OC$_3$H$_7$; and Z is selected from the group comprising NH$_2$, NHR, NR$_2$, and NR$_3$, wherein R is an alkyl or arylalkyl substituent.

In still another preferred embodiment, the invention includes a compound having the formula:

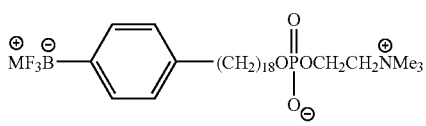
70 wherein M is selected from the group consisting of Li, Na, K, Cs and Rb and the compound is an intermediate in the synthesis of the boronic ester of the phospholipid ether analogs disclosed and claimed herein.

In yet another exemplary embodiment, the invention includes a method of synthesizing a high specific activity phospholipid ether (PLE) or alkyl phosphocholine (APC) analog, including the steps of:
(a) coupling an ester of diboron with a PLE or APC analog in the presence of a catalyst to result in a boronic acid or ester PLE or APC analog;
(b) optionally, esterifying the boronic acid of the PLE analog with 1,2- or 1,3-diols to result in the boronic esters of PLE or APC analog to step (a); and
(c) optionally, reacting the boronic acid or ester of PLE or APC analog of step (a) or (b) with sodium radiohalide, in the presence of an oxidant to result in a high specific activity radiohalogenated PLE or APC analog.

In some embodiments, the coupling reaction of step (a) is carried out with methanol as a solvent at temperatures of about 15-70° C. in the presence of a Pd catalyst. In still other versions, the in step (c) the oxidant is selected from the group consisting of: dichloramine-T; chloramine-B, dichloramine-B; iodogen, iodogen coated tubes, iodobeads, N-chlorosuccinimide; hydrogen peroxide, peracetic acid, m-chloro-perbenzoic acid and peroxidase. In other embodiments, the catalyst is

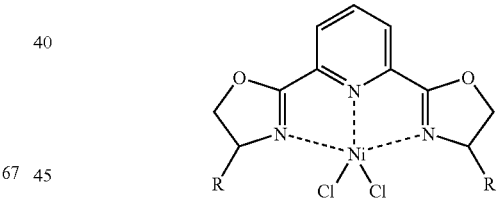

wherein R is selected from the group consisting of: H for Pybox, i-Pr for i-Pr-Pybox, s-Bu for s-Bu-Pybox, and Ph for Ph-Pybox.

In some preferred embodiments, the invention includes an intermediate in the synthesis having the structure:

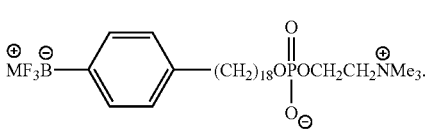
70

In this embodiment, M is selected from the group consisting of Li, Na, K, Cs and Rb.

In still another preferred embodiment, the invention includes a method of decreasing the growth of cancer wherein the method comprises administering to a patient in need thereof a boronic conjugate of a phospholipid ether analog; and administering radiation therapy to the patient. In this embodiment, cancer cells are bombarded by radiation thereby decreasing the growth of cancer. In some preferred embodiments, the radiation therapy is external beam radiation therapy or neutron capture therapy. Further, in various exemplary embodiments, the boronic ester of phospholipid ether analog has the structure:

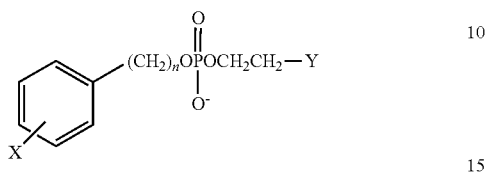

In this embodiment, X is selected from the group consisting of:

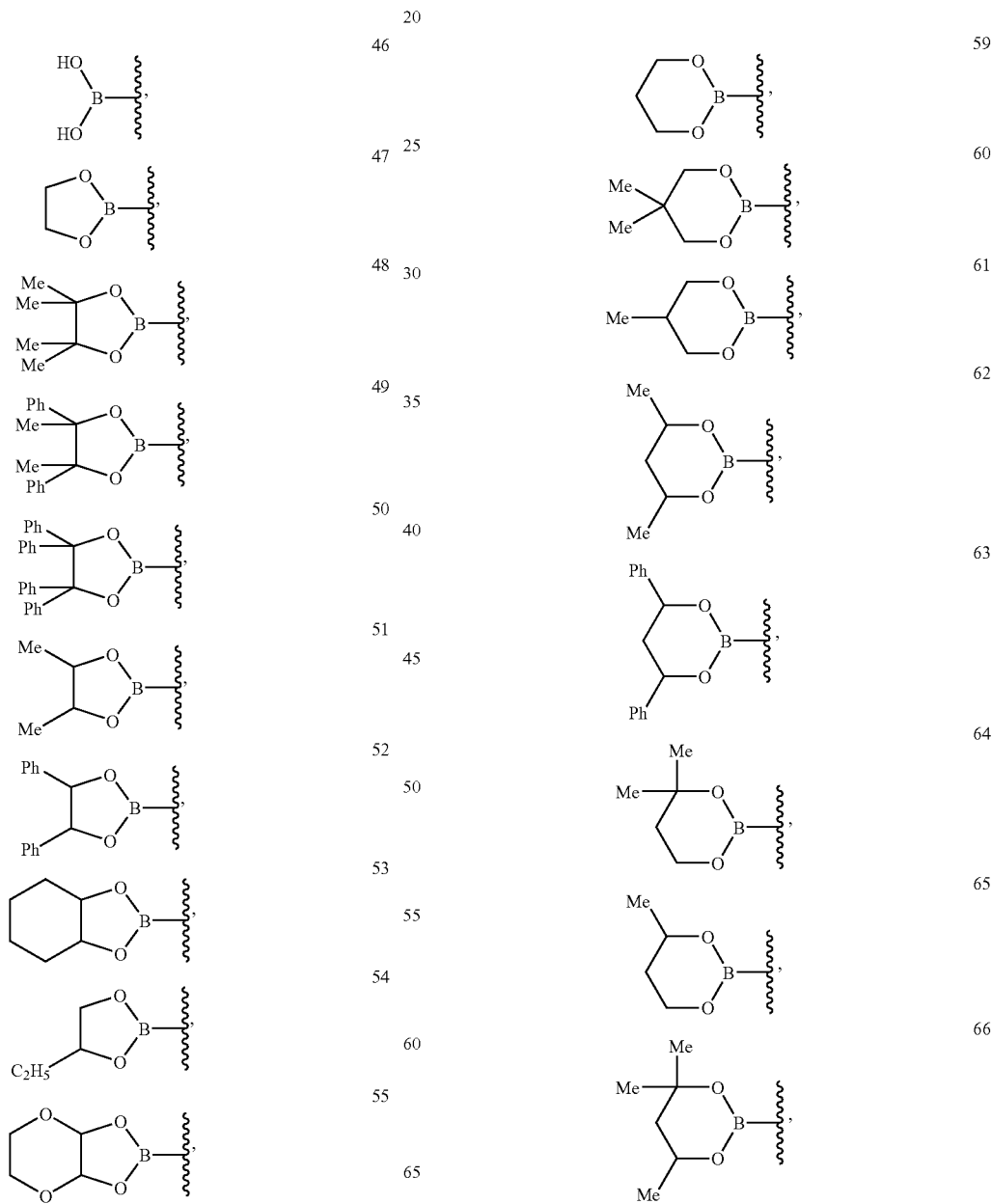

-continued

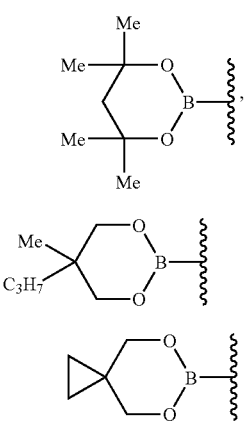

wherein n is an integer between 8 and 30; and Y is selected from the group comprising NH$_2$, NHR, NR$_2$, and NR$_3$, wherein R is an alkyl or arylalkyl substituent. In some preferred embodiments, the alkyl group has 1-3 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Further, the term "arylalkyl" group can be a benzene ring, and the alkyl group contains 1 to 3 carbon atoms.

In various preferred embodiments, the boronic acid or ester of the phospholipid analog has the structure:

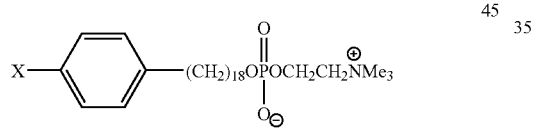

where X is selected from the group consisting of:

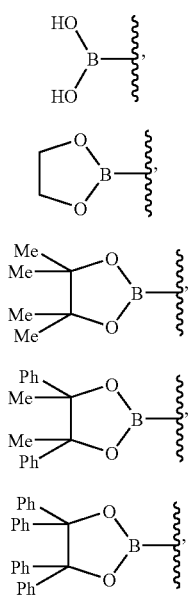

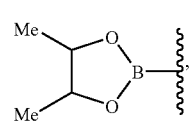

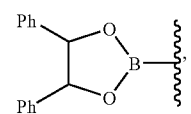

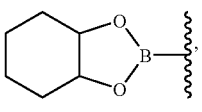

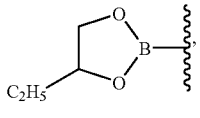

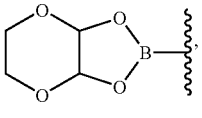

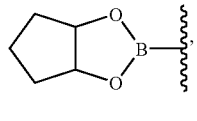

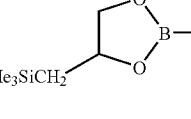

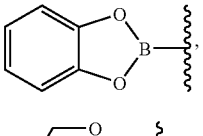

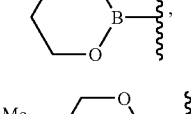

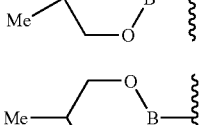

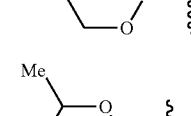

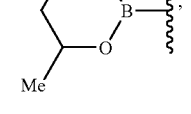

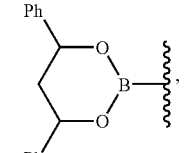

In various exemplary embodiments, the cancer is selected from a group consisting lung cancer, adrenal cancer, melanoma, colon cancer, colorectal cancer, ovarian cancer, prostate cancer, liver cancer, subcutaneous cancer, squamous cell cancer, adenocarcinoma, intestinal cancer, hepatocellular carcinoma, retinoblastoma, cervical cancer, glioma, breast cancer, pancreatic cancer, carcinosarcoma, hepatoma and carcinosarcoma.

Other objects, features and advantages of the present invention will become apparent from the following detailed description. It should be understood, however, that the detailed description and the specific examples, while indicating exemplary embodiments of the invention, are given by way of illustration only, since various changes and modifications within the spirit and scope of the invention will become apparent to those skilled in the art from the detailed description

BRIEF DESCRIPTION OF THE DRAWINGS

Various exemplary embodiments of the compounds and methods according to this invention will be described in detail with reference to the following figures, wherein;

In FIG. 3, control animals show rapidly growing tumors over the 10-week assessment period. This confirms that the compound itself C-NM404 has no substantial effect on tumor growth. The 50 and 150 μCi dose groups did not show any difference when compared to control animals, hence these seem to be ineffective dose levels in this animal model. However, the 250 and 500 μCi dose groups show a substantial and prolonged treatment effect. Tumor volumes are stable and some tumors appear "collapsed" (the tumor surface has collapsed). Additionally, hair above the tumors fell off confirming substantial accumulation of radioactivity in these tumors. The results show a dose-linear effect of $^{125}$I-NM404 on tumor volume. ● Control, C-NM404;

FIG. 8A, bioscan image obtained 4 days post $^{125}$I-NM404 injection into an ApcMin mouse. FIG. 8B is a digital photo and FIG. 8C is a positionally matched fused image of excised mouse lung containing spontaneous lung tumor (2 mm dia, arrow) showing intense uptake of NM404 into the tumor;

DETAILED DESCRIPTION OF THE EXEMPLARY EMBODIMENTS

Figure 1:
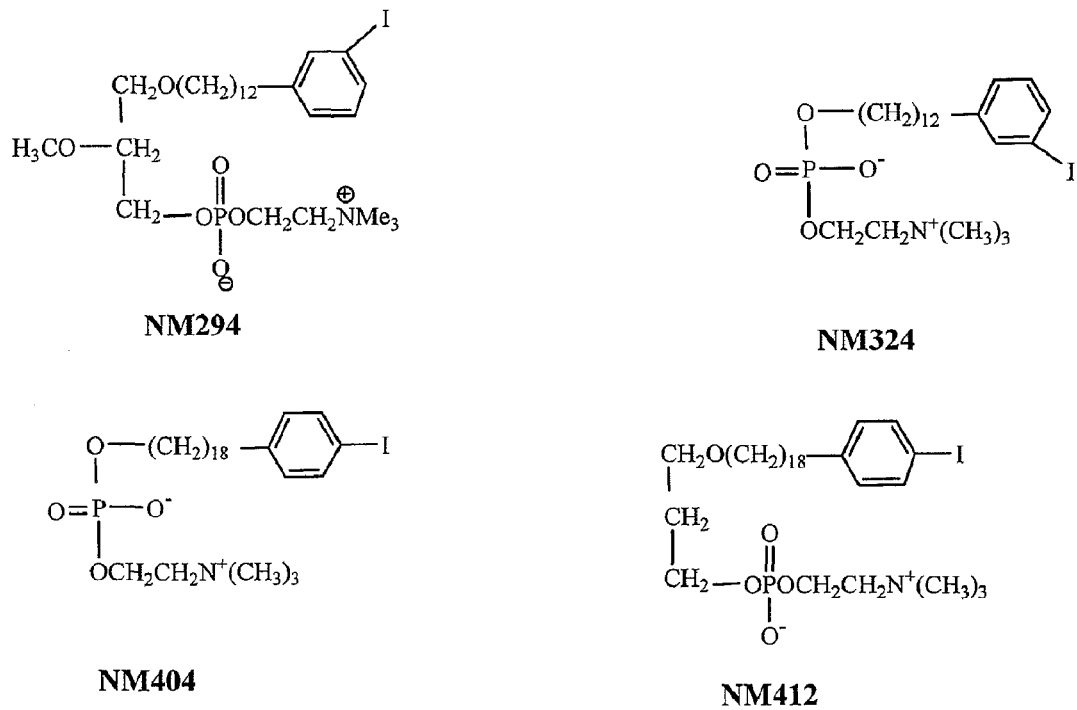
FIG. 1 illustrates exemplary structures of some phospholipid ether analog compounds according to the invention.

The present invention discloses boronic acids or esters of phospholipid ether and alkyl phosphocoline analogs and methods for their synthesis and use. The boronic acids or esters of the phospholipid ether and alkyl phosphocoline analogs disclosed herein can be used in treating cancer and in particular can be used in conjunction with radiation therapy, such as external beam radiation therapy and neutron capture therapy to specifically target and kill cancer cells.

Other objects, features and advantages of the present invention will become apparent from the following detailed description. It should be understood, however, that the detailed description and the specific examples, while indicating exemplary embodiments of the invention, are given by way of illustration only, since various changes and modifications within the spirit and scope of the invention will become apparent to those skilled in the art from the detailed description Before the present compounds and methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to optical isomers and analogs, structural isomers and analogs, conformational isomers and analogs, and the like. In one embodiment, this invention encompasses the use of different optical isomers of various PLE compounds. It will be appreciated by those skilled in the art that the PLE compounds useful in the present invention may contain at least one chiral center. Accordingly, the compounds used in the methods of the present invention may exist in, and be isolated in, optically-active or racemic forms. Some compounds may also exhibit polymorphism. As used herein "boron" refers to the chemical element with an atomic number of 5 and has the chemical symbol "B". Boron in a trivalent metalloid element found in the ore borax. Boron has two naturally-occurring and stable isotopes $^{11}$B and $^{10}$B and there are 13 known isotopes of boron. Unless otherwise noted the reference to element symbol "B" shall refer to all isotopes of boron whether known or unknown that are usable in the invention.

As used and discussed herein the term Pybox refers to a ligand family, disclosed, for example by H. Nishiyama, "Chiral and C$_2$-Symmetrical Bis(oxazolinylpyridine) rhodium(III) Complexes: Effective Catalysts for Asymmetric Hydrosilylation of Ketones," Organometallics, Vol. 8, No. 3, pp. 846-48 (March 1989). This catalyst has been successfully applied to the catalysis of asymmetric reactions. The two R groups on the oxazoline rings of PYBOX form a highly enantioselective "chiral fence," which enables better differentiation of the Re and Si faces of incoming substrates. as used herein such as, for example, i-Pr-Pybox, s-Bu-Pybox and Ph-Pybox refers to a PYBOX catalyst wherein i-Pr is iso-propyl, s-Bu is sec-butyl, Ph is phenyl and H is Pybox.

It is to be understood that the present invention may encompass the use of any racemic, optically-active, polymorphic, or stereoisomeric form, or mixtures thereof, which possess properties useful in the treatment of tumor-related conditions described and claimed herein. In one embodiment, the anti-tumor compounds may include pure (R)-isomers. In another embodiment, the anti-tumor compounds may include pure (S)-isomers. In another embodiment, the compounds may include a mixture of the (R) and the (S) isomers. In another embodiment, the compounds may include a racemic mixture comprising both (R) and (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

"Subject" or "patient" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" or "patient" does not denote a particular age or sex.

As used herein, "administering" or "administration" includes any means for introducing cancer therapeutics, including radiotherapy and chemotherapy, into the body, preferably into the systemic circulation. Examples include but are not limited to oral, buccal, sublingual, pulmonary, transdermal, transmucosal, as well as subcutaneous, intraperitoneal, intravenous, and intramuscular injection.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

As herein disclosed, the inventors have realized that by combining the tumor specificity of PLE compounds with radiation therapy, such as, boron neutron capture therapy (BNCT) or external beam radiation, cancer cells can be specifically targeted and destroyed with negligible effect on non-cancerous cells. Therefore, as described herein, in one embodiment, the invention comprises boronic esters of phospholipid compounds that can be used to specifically target cancer cells and localize radiation generated during radiation therapy, such as, neutron capture and external beam radiation therapy to cancerous tissue.

Therefore, in one exemplary embodiment, the invention includes boronic acids or esters of a phospholipid ether analog having the structure:

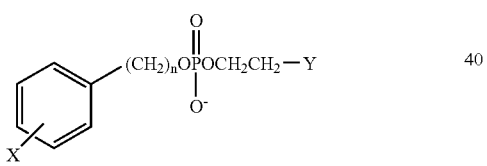

wherein X is selected from the group consisting of:

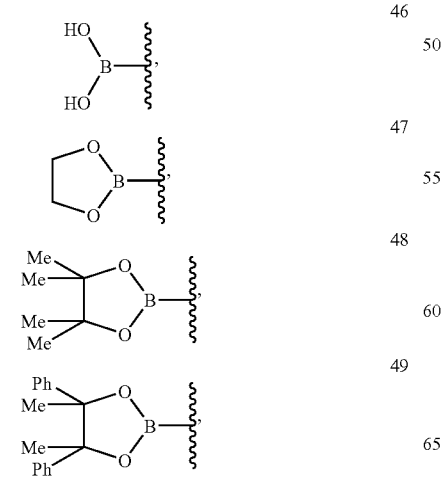

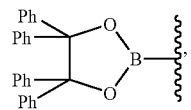

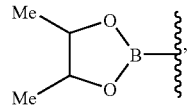

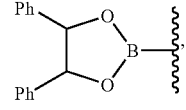

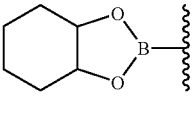

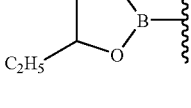

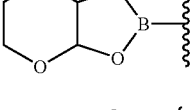

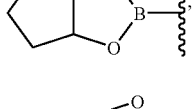

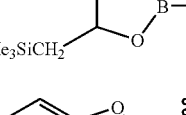

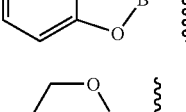

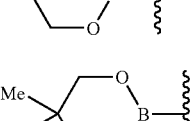

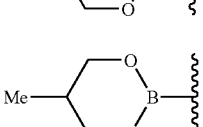

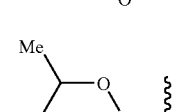

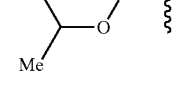

-continued
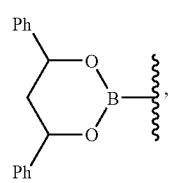
63
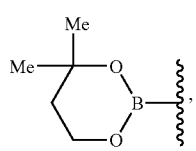
64
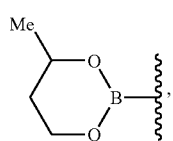
65
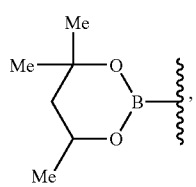
66
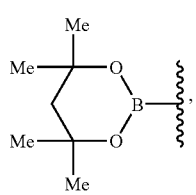
67
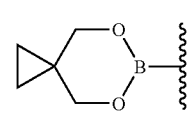
68
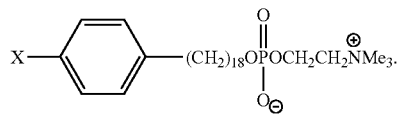
and
69
wherein n is an integer between 8 and 30; and Y is selected from the group comprising NH$_2$, NHR, NR$_2$, and NR$_3$, wherein R is an alkyl or arylalkyl substituent,
In some preferred embodiments, the boronic acid or ester of the phospholipid ether analog has the formula:
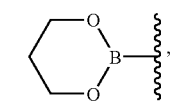
45
In these embodiments, X is selected from the group consisting of:
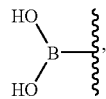
46
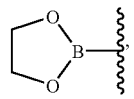
47
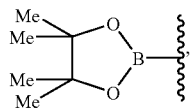
48
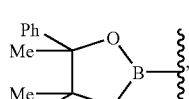
49
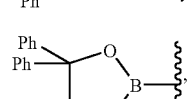
50
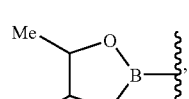
51
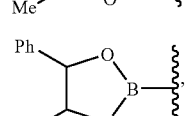
52
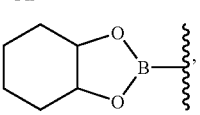
53
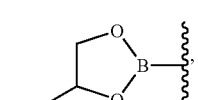
54
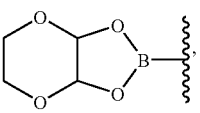
55
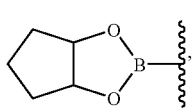
56
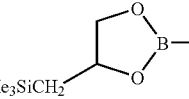
57
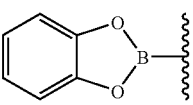
58
59

-continued
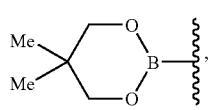
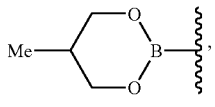
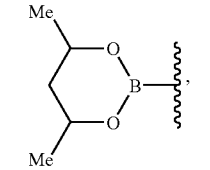
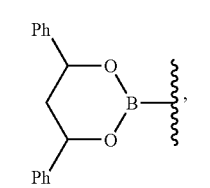
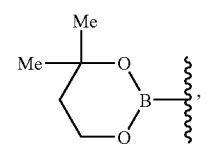
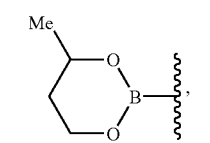
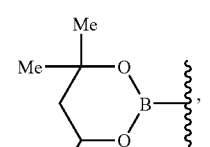
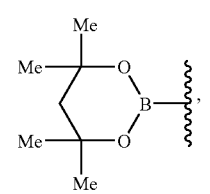
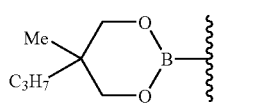 and
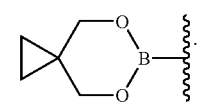
In yet another exemplary embodiment, the invention includes a boronic acid or ester of a phospholipid ether analog having the structure:
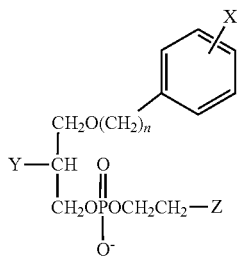
wherein X is selected from the group consisting of:
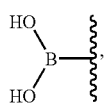
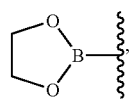
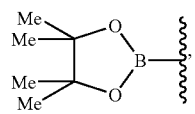
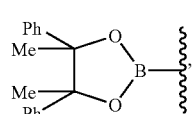
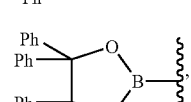
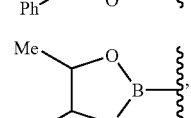
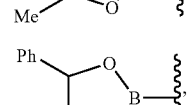
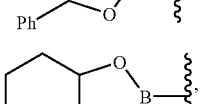
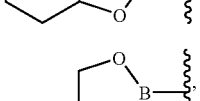
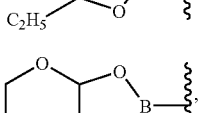
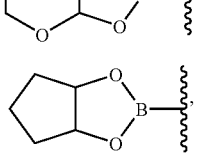

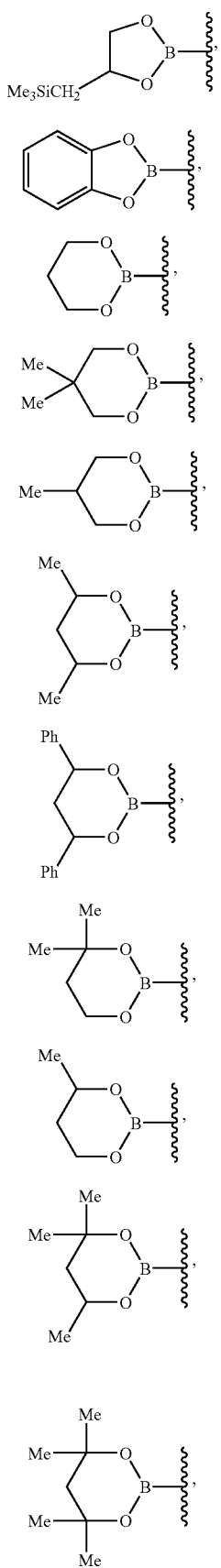

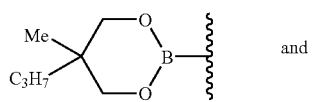

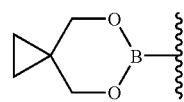

wherein n is an integer between 8 and 30; and Y is selected from the group consisting of H, OH, $OCH_3$, $OC_2H_5$, $OC_3H_7$; and Z is selected from the group comprising $NH_2$, NHR, $NR_2$, and $NR_3$, wherein R is an alkyl or arylalkyl substituent.

In still another preferred embodiment, the invention includes a compound having the formula:

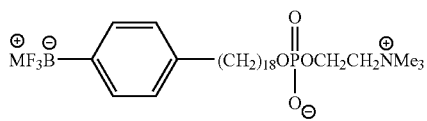

wherein M is selected from the group consisting of Li, Na, K, Cs and Rb and the compound is an intermediate in the synthesis of the boronic ester of the phospholipid ether analog disclosed herein.

In yet another exemplary embodiment, the invention includes a method of synthesizing a high specific activity phospholipid ether (PLE) analog, including the steps of:
(a) coupling an ester of diboron with a PLE or APC analog in the presence of a catalyst to result in a boronic acid or ester PLE or APC analog;
(b) optionally esterifying the boronic acid of the PLE analog with 1,2- or 1,3-diols to result in the boronic esters of PLE or APC analog to step (a); and
(c) optionally, reacting the boronic acid or ester of PLE or APC analog of step (a) or (b) with sodium radiohalide, in the presence of an oxidant to result in a high specific activity radiohalogenated PLE or APC analog.

In some versions, the coupling reaction of step (a) is carried out with methanol as a solvent at temperatures of about 15-70° C. in the presence of a Pd catalyst. In still other versions, the in step (c) the oxidant is selected from the group consisting of: dichloramine-T; chloramine-B, dichloramine-B; iodogen, iodogen coated tubes, iodobeads, N-chlorosuccinimide; hydrogen peroxide, peracetic acid, m-chloro-perbenzoic acid and peroxidase. In other embodiments, the catalyst is:

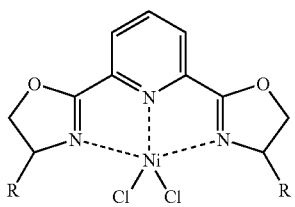

wherein R is selected from the group consisting of: H for Pybox, i-Pr for i-Pr-Pybox, s-Bu for s-Bu-Pybox, and Ph for Ph-Pybox. In some preferred embodiments, the invention includes an intermediate in the synthesis having the structure:

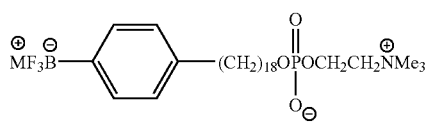

70

In this embodiment, M is selected from the group consisting of Li, Na, K, Cs and Rb.

In still another preferred embodiment, the invention includes a method of decreasing the growth of cancer wherein the method comprises administering to a patient in need thereof a boronic conjugate of a phospholipid ether analog; and administering radiation therapy to the patient. In this embodiment, cancer cells are bombarded by radiation thereby decreasing the growth of cancer. In some preferred embodiments, the radiation therapy is external beam radiation therapy or neutron capture therapy. Further, in various exemplary embodiments, the boronic conjugate of phospholipid ether analog has the structure:

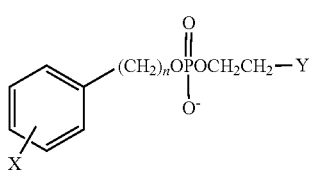

In this embodiment, X is selected from the group consisting of:

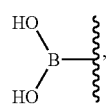 46

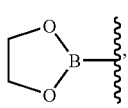 47

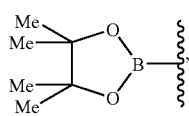 48

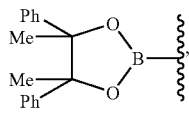 49

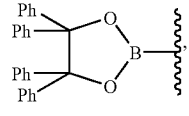 50

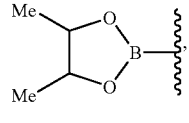 51

-continued

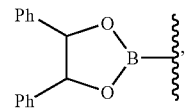 52

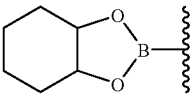 53

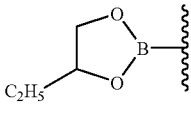 54

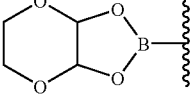 55

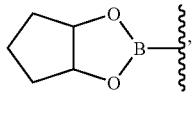 56

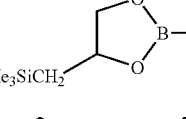 57

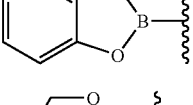 58

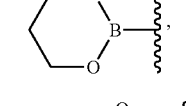 59

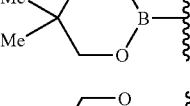 60

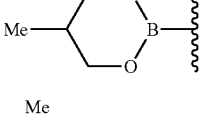 61

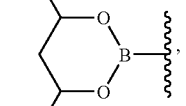 62

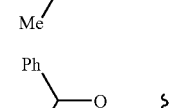 63

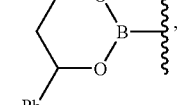 64

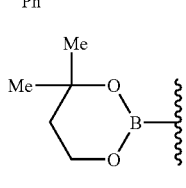

-continued

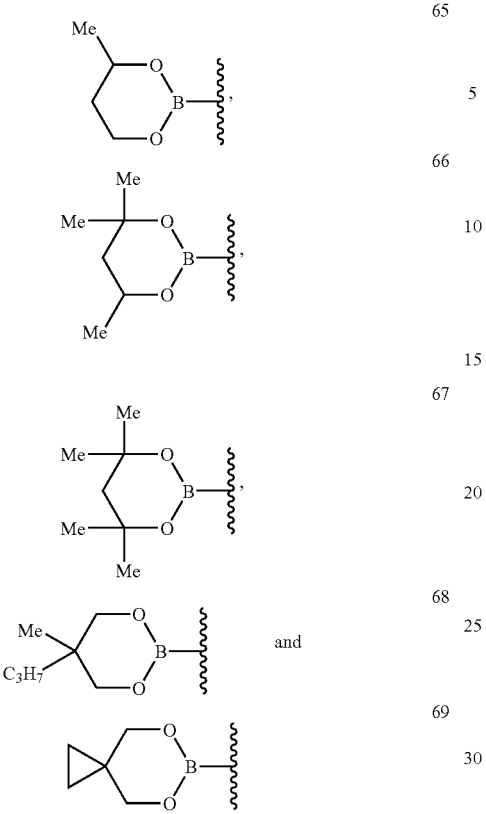

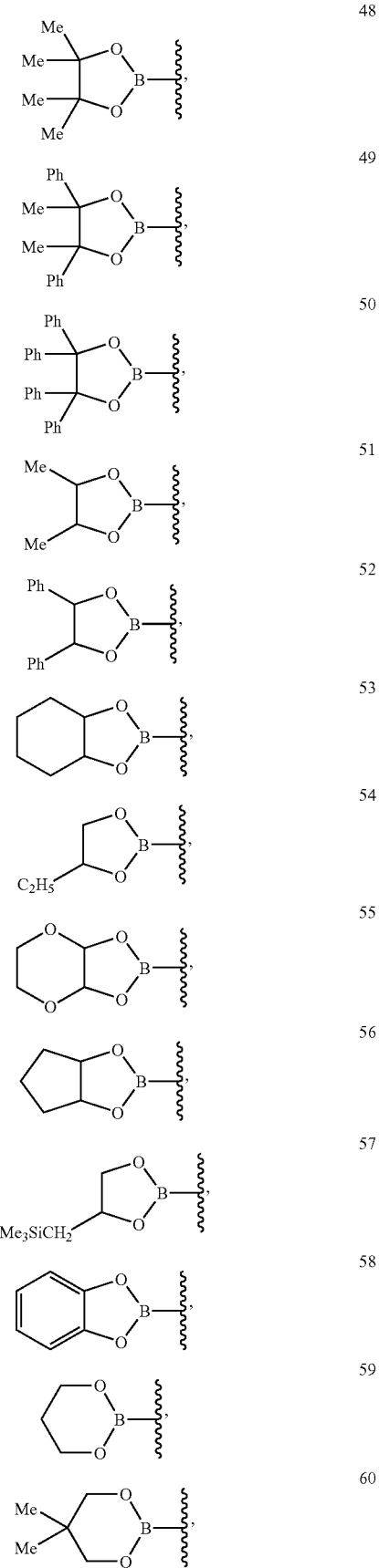

wherein n is an integer between 8 and 30; and Y is selected from the group comprising NH$_2$, NHR, NR$_2$, and NR$_3$, wherein R is an alkyl or arylalkyl substituent. In some preferred embodiments, the alkyl group has 1-3 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Further, the term "arylalkyl" group can be a benzene ring, and the alkyl group contains 1 to 3 carbon atoms.

In various preferred embodiments, the boronic conjugate of the phospholipid ether analog is an ester having the structure:

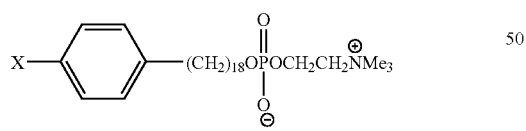

where X is selected from the group consisting of:

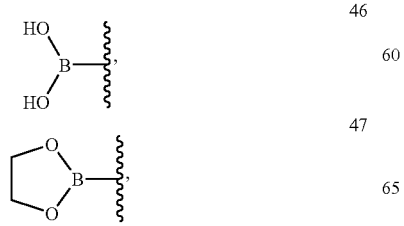

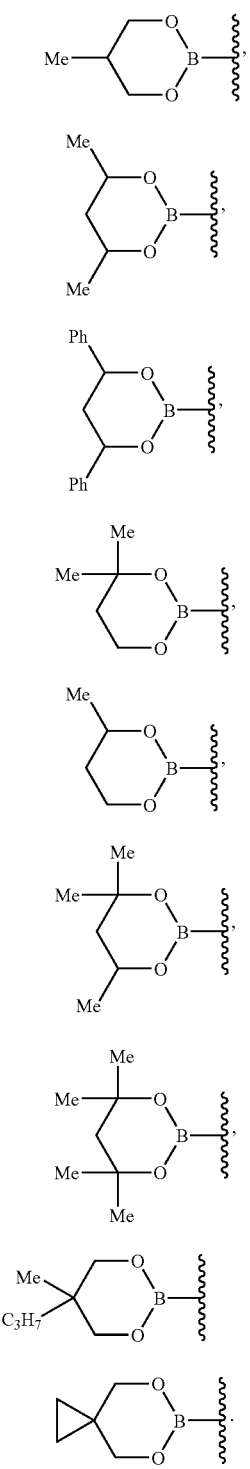

In various exemplary embodiments, the cancer is selected from a group consisting lung cancer, adrenal cancer, melanoma, colon cancer, colorectal cancer, ovarian cancer, prostate cancer, liver cancer, subcutaneous cancer, squamous cell cancer, adenocarcinoma, intestinal cancer, hepatocellular carcinoma, retinoblastoma, cervical cancer, glioma, breast cancer, pancreatic cancer, carcinosarcoma, hepatoma and carcinosarcoma.

PLE Tumor Specificity

The utility of tumor tracers like $^{67}$Ga-citrate and $^{18}$F-FDG is limited by their lack of specificity to distinguish neoplasm from inflammation. Further, accumulation of FDG in the urine interferes with visualization of pelvic and abdominal abnormalities. This lack of specificity is a significant clinical issue in patients with cancer. However, studies with PLE analogs shows they can overcome this limitation. Some exemplary embodiments of PLE analogs discussed herein are illustrated in FIG. 1. Previous experiments conducted by the inventors in rats revealed no uptake and retention of NM324 into carrageenan-induced granulomas. Gallium citrate, however, utilized as a control in this study, did indeed concentrate significantly in the granulomatous lesions. This preliminary finding, that PLE analogs did not apparently localize in inflammatory lesions encouraged the inventors to further evaluate this class of agents in human cancer patients. Although FDG-PET has paved the way for hybrid imaging, its lack of tumor cell specificity will always limit its diagnostic efficacy. New molecularly targeted agents, like NM404, which display universal tumor uptake and selective retention regardless of location, as well as selectivity for malignant tumor cells and not inflammatory or hyperplastic lesions, represents a significant improvement in the detection, targeting and characterization of cancer.

While planar nuclear medicine imaging techniques have historically afforded acceptable 2D images, this modality offers no tomographic capability and poor image quantitation. Previously, $^{125}$I-NM404 was investigated for its use in scintigraphic imaging and tissue distribution studies in rodent tumor models and $^{131}$I was suitable for Phase 1 safety and pharmacokinetic evaluation in human lung cancer patients. However, neither are optimal for quantitative in vivo human imaging, see, for example, U.S. patent application Ser. Nos. 10/906,687 and 11/177,749. PET imaging with iodine-124, a relatively new and commercially available positron isotope with a 4-day half-life, should alleviate many of the problems associated with planar imaging. Combining the unique tumor imaging capabilities of PLEs, such as, NM404 into PET scanning has now become a major goal of the inventors since iodine-124 has recently become commercially available.

Figure 2:
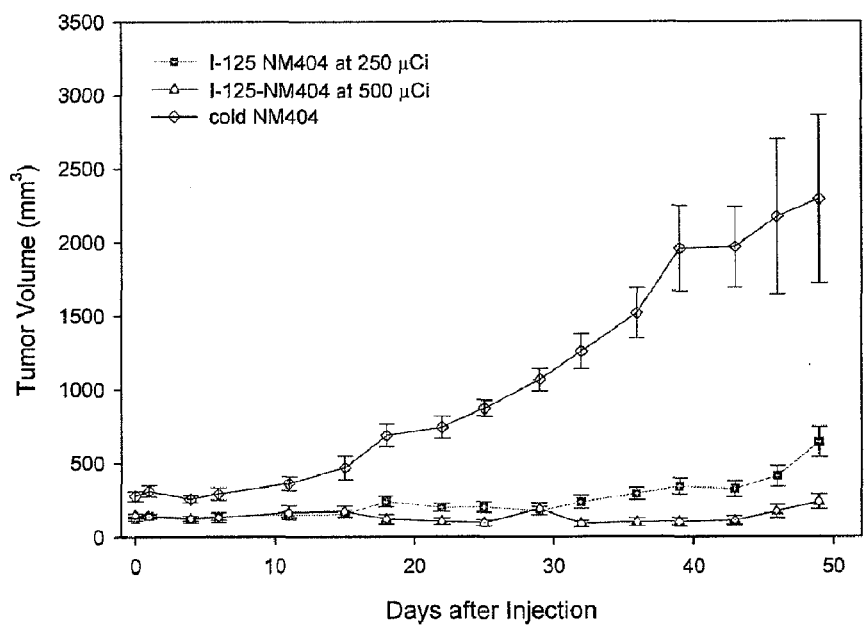
FIG. 2 illustrates the change in tumor volume following a single-dose treatment with $^{125}$I-NM404 at 250 μCi (■) and 500 μCi (▲) dose levels shows significant effects in inhibiting the progression of primary tumor growth in SCID mice bearing PC3 human prostate cancer xenografts. Tumor volumes were calculated using formula (width)$^2$×(length)/2 and expressed as mean±SEM, n=6 for each group. ◇ Cold NM404, control.
Figure 3:
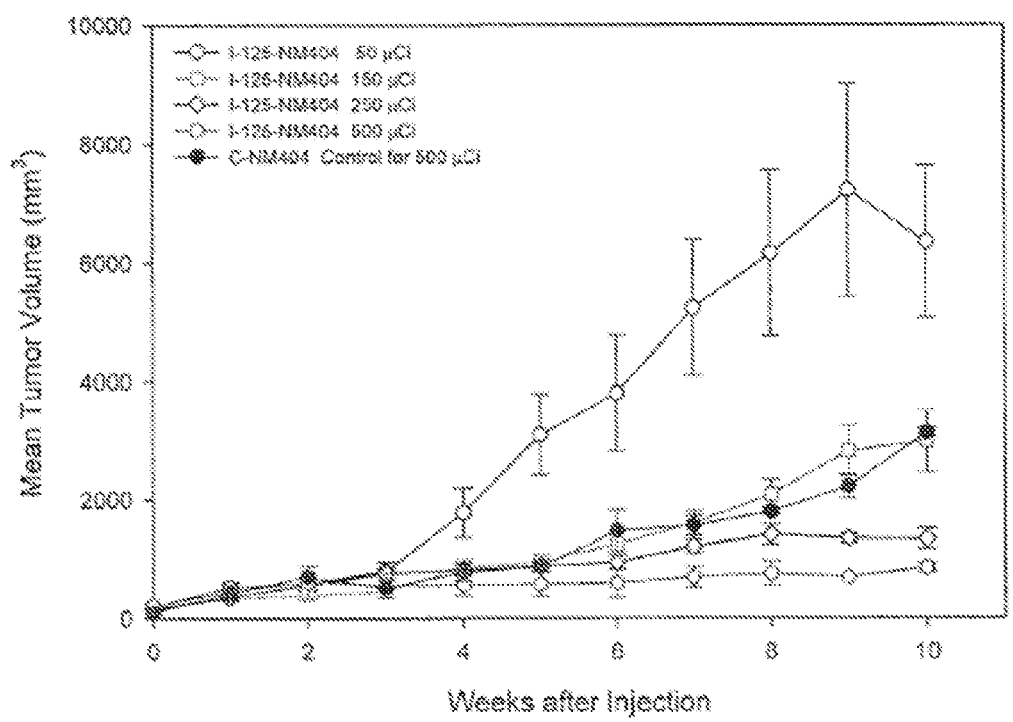
FIG. 3 illustrates antitumor effect of single-dose treatment with $^{125}$I-125-NM404 at doses of 50 (○), 150 (□), 250 (◇) and 500 (○) μCi in SCID mice bearing A549 human non-small cell lung cancer xenografts.
Figure 4:
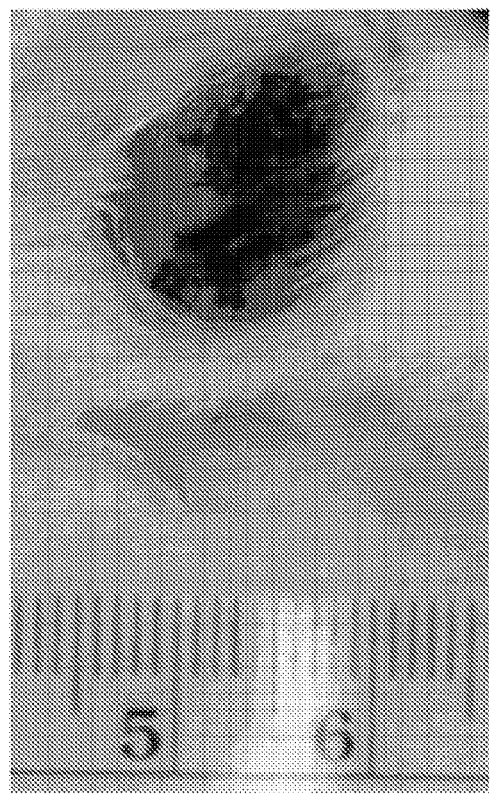
FIG. 4 is an image showing one of the tumor-bearing animals treated with 250 μCi of $^{125}$I-NM404 at 4 weeks following injection. The hair above the tumor has fallen off, apparently due to the significant accumulation of radioactivity in the tumor. Additionally, the surface of the tumors appears "caved in" and shows darker areas, presumably from hemorrhage and necrosis. The figure shows the effect of $^{125}$I-NM404 on the tumor. Although tumor size (outer dimensions) may not decrease, $^{125}$I-NM404 causes central necrosis. The measurement method for determining outer tumor dimensions may have underestimated tumor volume response following dosing with $^{125}$I-NM404.

The inventors have previously shown that $^{125}$I-labeled PLE analogs such as NM404 are effective in targeting tumor therapies to tumor cells following single injection and fractionated dosing. For assessment of efficacy of $^{125}$I-NM404 treatment, assessments of tumor volume were made until 10 weeks post-injection or until no animal in the control group was alive, whatever came first. Summarizing the results, control animals show rapidly growing tumors over the 10-week assessment period. See, FIGS. 2 and 3. This confirms that the unlabeled compound itself, NM404, has no substantial effect on tumor growth. The 50 µCi dose group did not show any difference when compared with control animals, hence these seem to be ineffective dose levels in this animal model. However, the 150, 250 and 500 µCi dose groups show a substantial and prolonged treatment effect. Tumor volumes are stable and the same tumors appear "collapsed" (the tumor surface has caved in). Additionally, the hair above the tumors fell off confirming substantial accumulation of radioactivity in these tumors, FIG. 4. The results show a dose-linear effect of $^{125}$I-NM404 on tumor volume. (See also, for example, U.S. patent application Ser. No. 11/671,403 hereby incorporated in its entirety for all purposes.)

In the above cases, the inventors identified the therapeutic effect of radiolabled PLE analogs. While such compounds are ideal for use due to their direct chemotherapeutic effect on tumor cells, due to their on-going research, the inventors have recognized the efficacy of boron conjugated analogs of PLE that are usable in radiotherapy, such as, for example, BNCT and external beam radiation therapy to treat cancer patients.

In such use, boron conjugated PLEs can be used in treating various cancers and cell types including but not limited to Lung cancer, Adrenal cancer, Melanoma, Colon cancer, Colorectal cancer, Ovarian cancer, Prostate cancer, Liver cancer, Subcutaneous cancer, Squamous cell cancer, Adenocarcinoma, Intestinal cancer, Hepatocellular carcinoma, Retinoblastoma, Cervical cancer, Glioma, Breast cancer, Pancreatic cancer, Carcinosarcoma, Hepatoma and Carcinosarcoma.

EXAMPLES

Methods of Synthesis of High Specific Activity PLE/APC Analogs

Generally this invention provides a method of synthesizing high specific activity phospholipid ether (PLE) analog, comprising the steps of:

to conjugate a stable isotope of boron, such as boron-10, to the PLE for concentration in tumor cells. The area of the tumor can then be bombarded with a beam of low-energy neutrons, for BNCT or gamma rays for external beam radiation therapy, thereby precisely delivering fatal doses of radiation directly to the neoplastic cells. Boron-10 or other suitable isotopes disintegrate after capturing a neutron and the high energy heavy charged particles produced destroy only the cells in close proximity to it, e.g., the cancer cells leaving adjacent, normal, cells unaffected.

Exemplary Synthesis of High Specific Activity NM404:

In the synthesis of high specific activity NM404 the inventors approach was based on the use of organoboron compounds as precursors to radiohalogenated pharmaceuticals. There are several methods for labeling molecules with radiohalogens via organometallic intermediates containing mercury, thallium, boron, silicon, germanium and lead (Kabalka, G. W.; Varma, R. S. The synthesis of radiolabeled compounds via organometallic intermediates. *Tetrahedron* 1989, 45, 6601-6621). Another aspect of the invention is illustrated in Scheme I.

Scheme I:

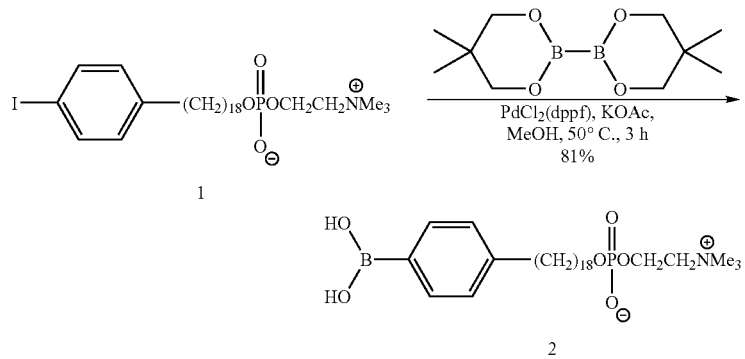

(a) coupling an ester of diboron with a PLE or APC analog in the presence of a catalyst to result in a boronic acid or ester PLE or APC analog;
(b) optionally esterifying the boronic acid of the PLE analog with 1,2- or 1,3-diols to result in the boronic esters of PLE or APC analog to step (a); and
(c) optionally, reacting the boronic acid or ester of PLE or APC analog of step (a) or (b) with sodium radiohalide, in the presence of an oxidant to result in a high specific activity radiohalogenated PLE or APC analog.

In the synthesis of high specific activity PLE analogs, such as NM404, the inventors have used organoboron compounds as precursors to radiohalogenated pharmaceuticals. There are several methods for labeling molecules with radiohalogens via organometallic intermediates containing mercury, thallium, boron, silicon, germanium, tin and lead. Among these organometallics, organoboron compounds are used in radioiodination because they are stable, easy to handle, have low toxicity (as compared to organotin, organolead or organomercury compounds) and generally give the radiolabeled product in a high yield. As disclosed herein, the inventors have synthesized boronic esters of PLE. Due to the unique characteristics of PLE to target only cancer cells and, combined with the unique properties of boron as used in neutron capture therapy, the PLE-boronic esters disclosed provide a powerful compound for use in radiotherapy, including neutron capture therapy and external beam radiation therapy. In effect, the boronic ester compounds disclosed herein allow the inventors In various exemplary embodiments, the $PdCl_2$ catalyst has the structure:

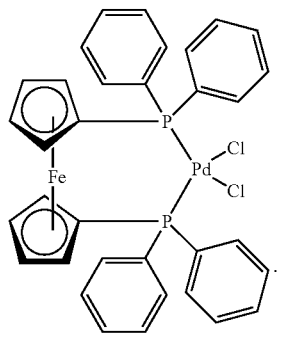

In the case of the neopentyl glycol ester, the neopentyl moiety did not survive the conditions of chromatography in the $CHCl_3$-MeOH—$H_2O$ solvent system, and the product was obtained as a boronic acid 2. A pinacol ester was more stable towards hydrolysis, and pinacol boronic ester 3 could be isolated in the reaction of NM404 with bis-(pinacolato) diboron. This reaction is shown in Scheme II. Pinacol ester 3 was also obtained by esterification of borono-NM404 (2) with pinacol, and this two steps procedure is a preferred method since the product has higher purity (Scheme III). Conditions of cross-coupling reaction were optimized and the amount of catalyst $PdCl_2$(dppf) was in the range of 1-5%.

Scheme II:
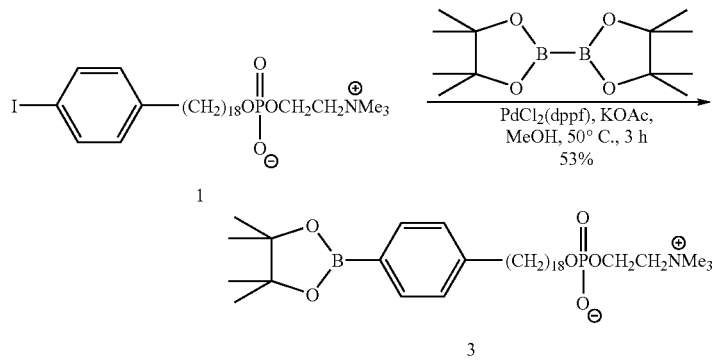
Scheme III:
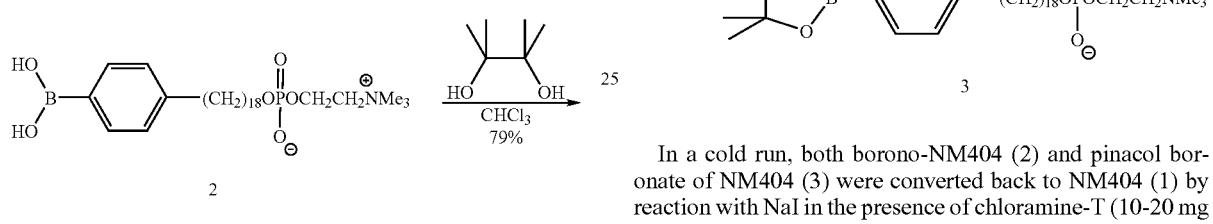
In a cold run, both borono-NM404 (2) and pinacol boronate of NM404 (3) were converted back to NM404 (1) by reaction with NaI in the presence of chloramine-T (10-20 mg scale) in about 90% yield (Scheme IV).
Scheme IV:
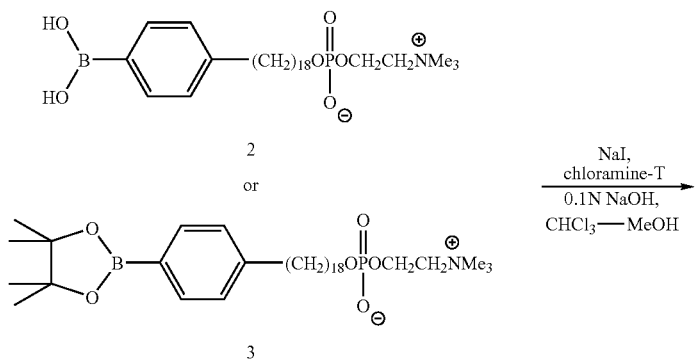
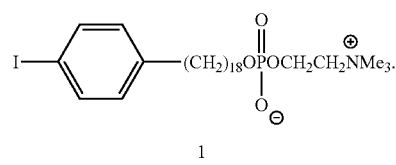

Dihydroxyboryl compound 2 was converted into $^{125}$I-NM404 according to Scheme V. Chloramine-T served as an oxidant and the solvent was the mixture of ethanol and 0.1 N hydrochloric acid. The radiochemical yield was in the range of 40-50%, the radiochemical purity was 92-98%.

Scheme IV:

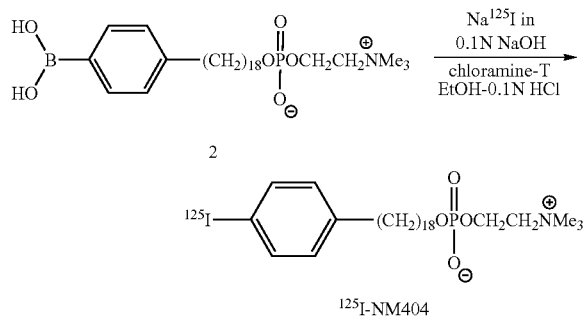

$^{125}$I-NM404

A 0.5 ml-V-vial was charged with 18-[p-(dihydroxyboryl)-phenyl]-octadecyl phosphocholine (50 µl of 1 mg ml solution in EtOH) followed by addition of a solution of I-[125] sodium iodide (700 µCi, 2 µl) in 0.1 N aqueous NaOH. Chloramine-T in the mixture of EtOH—0.1 N aq HCl (8:2) (50 µl of 1 mg/ml) was added and the reaction mixture was maintained at room temperature for 45 min. Solvents were removed under a stream of nitrogen and the residue was redissolved in abs. EtOH (100 µl) prior to HPLC purification. Preparative HPLC purification was performed using a silica gel cartridge column (3 cm/3 µm) and isopropanol-hexane-water (52:40:8) mixture as the mobile phase. The product was collected using a radiodetector. Radiochemical yield: 320 µCi (46%).

General Materials and Reagents:

Unless otherwise indicated, all chemicals were purchased from Aldrich Chemical Co. (Milwaukee, Wis.). Thin-layer chromatography was performed using DC-Alufolien Kieselgel 60 $F_{254}$ plates (E. Merck, Darmstadt, Germany). Visualization was achieved by UV light and/or using cerium molybdate stain. NMR data were collected on a spectrometer. Chemical shifts are reported in parts per million (ppm) relative to tetramethylsilane (TMS), and spin multiplicities are given as s (singlet), d (doublet), t (triplet), q (quartet), m (multiplet) or br m (broad multiplet). High-resolution mass spectra were obtained using MALDI FT-Mass Spectrometer analysis.

Example 1

18-[p-(Dihydroxyboryl)phenyl]octadecyl phosphocholine (2)

NM404 (72 mg, 0.113 mmol), bis-(neopentylglycolato) diboron (60 mg, 0.266 mmol), anhydrous potassium acetate (34 mg, 0.346 mmol) and $PdCl_2$(dppf) (5 mg, 0.0061 mmol) were placed in a 4 ml vial and dried under high vacuum for 30 min. The vial was filled with nitrogen and methanol (1.5 ml, degassed by three freeze-pump-thaw cycles) was added. Reaction mixture was stirred at 50° C. for 2 h, then evaporated, redissolved in chloroform and loaded onto silica gel column. The column was eluted first with stepwise gradient of $CHCl_3$-MeOH (90:10, 80:20, 50:50) and finally with $CHCl_3$-MeOH—$H_2O$ (65:25:4) to give the product as a white powder, 51 mg (81%). $^1$H-NMR (400 MHz, $CDCl_3$—$CD_3OD$ 1:1): 7.53 and 7.19 (two d, J=8 Hz, 2H each, $C_6H_4$), 4.26-4.20 (br m, 2H, $POCH_2CH_2N$), 3.87 (q, J=6.6 Hz, 2H, $CH_2OPOCH_2CH_2N$), 3.61-3.58 (m, 2H, $CH_2N$), 3.22 (s, 9H, $N(CH_3)_3$), 2.61 (t, J=7.7 Hz, 2H, $ArCH_2$), 1.68-1.58 (m, 4H, $ArCH_2CH_2$ and $CH_2CH_2O$), 1.42-1.24 (m, 28H, $(CH_2)_{14}$). $^{13}$C-NMR (100 MHz, $CDCl_3$—$CD_3OD$ 1:1)*: 144.82, 133.54, 127.93, 66.55 (m), 66.00 (d, $J_{C-P}$=5.8 Hz), 58.95 (d, $J_{C-P}$=5.1 Hz), 54.03 (t, $J_{C-N}$=3.9 Hz), 36.03, 31.43, 30.85 (d, $J_{C-P}$=7.6 Hz), 29.75 (four carbons), 29.71 (five carbons), 29.63, 29.54, 29.47, 29.33, 25.88. *Due to the quadrupolar relaxation, the carbon attached to boron is not detected.

Example 2

18-[4-(4,4,5,5-Tetramethyl-[1,3,2]dioxaborolan-2-yl)-phenyl]-octadec-1-yl phosphocholine (3)

Method A: NM404 (51 mg, 0.080 nmol), bis-(pinacolato) diboron (49 mg, 0.192 mmol), anhydrous potassium acetate (24 mg, 0.24 mmol) and $PdCl_2$(dppf) (1.3 mg, 0.0016 mmol) were placed in a 4 ml vial and dried under high vacuum for 30 min. Vial was filled with nitrogen and methanol (1.5 ml, degassed by three freeze-pump-thaw cycles) was added. Reaction mixture was stirred at 50° C. for 2.5 h, then evaporated, redissolved in chloroform and loaded onto silica gel column. The column was eluted first with stepwise gradient of $CHCl_3$-MeOH (90:10, 80:20, 50:50) and finally with $CHCl_3$-MeOH—$H_2O$ (65:25:4) to give the product as a white powder, 27 mg (53%). $^1$H-NMR (400 MHz, $CDCl_3$—$CD_3OD$ 1:1): 7.69 and 7.20 (two d, J=7.8 Hz, 2H each, $C_6H_4$), 4.26-4.20 (br m, 2H, $POCH_2CH_2N$), 3.87 (q, J=6.6 Hz, 2H, $CH_2OPOCH_2CH_2N$), 3.61-3.58 (m, 2H, $CH_2N$), 3.22 (s, 9H, $N(CH_3)_3$), 2.62 (t, J=7.7 Hz, 2H, $ArCH_2$), 1.68-1.58 (m, 4H, $ArCH_2CH_2$ and $CH_2CH_2O$), 1.36 (s, 12H, pinacol $CH_3$ groups), 1.42-1.24 (m, 28H, $(CH_2)_{14}$). $^{13}$C-NMR (100 MHz, $CDCl_3$—$CD_3OD$ 1:1)†: 147.12, 135.23, 128.43, 84.36, 66.97 (m), 66.42 (d, $J_{C-P}$=5.8 Hz), 59.39 (d, $J_{C-P}$=5.1 Hz), 54.43 (t, $J_{C-N}$=3.9 Hz), 36.62, 31.85, 31.28 (d, $J_{C-P}$=7.7 Hz), 30.18 (three carbons), 30.16 (two carbons), 30.14 (three carbons), 30.11, 30.05, 29.96, 29.89, 29.74, 26.30, 24.99. HRMS calculated for $C_{35}H_{65}BNO_6P$ (M$^+$+H): 638.4721. Found 638.4660. †Due to the quadrupolar relaxation, the carbon attached to boron is not detected.

Method B: Compound 2 (50 mg, 0.09 mmol) and pinacol (21 mg, 0.18 mmol) were suspended in $CHCl_3$ (3 ml) and stirred for 12 h at 40° C. During this time all solids dissolved. The reaction mixture was loaded onto silica gel column. The column was eluted first with stepwise gradient of $CHCl_3$-MeOH (90:10, 80:20, 50:50) and finally with $CHCl_3$-MeOH—$H_2O$ (65:25:4) to give the product as a white powder, 45 mg (79%).

Using chloramine-T has one disadvantage associated with formation of tosyl-containing byproducts. Since it is known that chloramine-T forms HOCl in aqueous solutions, hypochlorite is likely the active intermediate that generates electrophilic iodine species. In this regard, it may be feasible to use bleach (aqueous NaOCl solution) instead of chloramine-T. High specific activity radio halogenated compounds may be produced as described above in the cold run by one of ordinary skill in the art.

Example 3

Improved Synthesis of Long Chain ω-(p-Iodophenyl)alkyl Alcohols and Corresponding Phospholipid Ethers and Alkyl Phosphocholines Including NM404

Previous reports from the laboratories of R. E. Counsell and J. P. Weichert described the remarkable capacity of radioiodinated phospholipid (PLE) and alkyl phosphocholine (APC) analogs NM294, NM324, NM404 and NM412 (FIG. 1) to be selectively retained by a variety of human and animal tumors in xenograft and spontaneous tumor rodent models.

The reason for the retention of PLE and analogs in cancer cells remains unknown. Without being held to any particular theory, however, the prevailing hypothesis, is that radioiodinated PLE and APC analogs become trapped in tumor cell membranes because of their inability to be metabolized and eliminated. On the other hand, such lipid molecules are metabolized and cleared by normal tissues, including the liver. Support for this hypothesis was found when lipid extraction of tumors following administration of radioiodinated PLE to tumor bearing animals showed only the presence of the intact agent, whereas similar analysis of urine and feces revealed only the presence of metabolites.

The main challenge in the synthesis of PLE and APC analogs containing the conjugated phenyl group is the synthesis of long chain ω-(p-iodophenyl)alkyl alcohols. The inventors have recently published a synthesis of a series of PLE and APC analogs having 12, 15 and 18 methylene groups in the alkyl chain (Pinchuk A N, Rampy M A, Longino L A, Skinner R S, Gross M D, Weichert J P, Counsell R E. *J. Med. Chem.* 2006; 49: 2155-2165). The synthetic strategy was based on the cross-coupling reaction of Grignard reagents with alkyl tosylates or halides catalyzed by $Li_2CuCl_4$ at −78° C. Unfortunately, the coupling product was often contaminated with de-iodo impurity which resulted from iodine-magnesium exchange, the known reaction between aryl iodides and alkyl Grignard reagents. Removal of de-iodo impurity required multiple crystallization steps which led to the partial loss of the product. This method also suffered from moderate yield (30-50%) in the cross-coupling step.

Recent developments in the field of transition metal-catalyzed cross-coupling reaction for $sp^3$-$sp^3$ carbon-carbon bond formation from organic electrophiles and organometallic nulceophiles make it possible to design a new synthetic route and solve existing problems. Organozinc reagents are a better alternative to organomagnesium (Grignard) reagents because organozincs are highly functional-group tolerant and can be generated under mild conditions. G. C. Fu (Fischer C, Fu G C. *J. Am. Chem. Soc.* 2005; 127: 4594-4595; Arp F O, Fu G C. *J. Am. Chem. Soc.* 2005; 127: 10482-10483) has recently described a powerful catalyst system (Ni(II)-Pybox complexes) for the cross-coupling reaction of non-activated primary and secondary alkyl bromides and iodides with alkyl zinc reagents. The catalyst (shown below) is a Ni(II) complex of 2,6-bis-(4-isopropyl-2-oxazolin-2-yl)-pyridine (1-Pr-Pybox) 71, 2,6-bis-(4-sec-butyl-2-oxazolin-2-yl)-pyridine (s-Bu-Pybox) 72 or 2,6-bis-(4-phenyl-2-oxazolin-2-yl)-pyridine (Ph-Pybox) 73 or pybox (H-Pybox) 74. The cross-coupling reaction can be performed at 0° C. or room temperature.

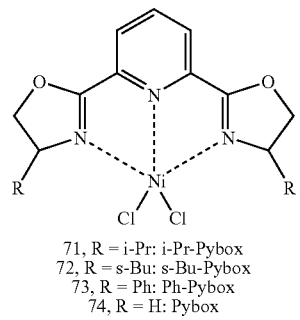

71, R = i-Pr: i-Pr-Pybox
72, R = s-Bu: s-Bu-Pybox
73, R = Ph: Ph-Pybox
74, R = H: Pybox This method opens the opportunity to synthesize 18-(p-iodophenyl)octadecanol 12 from various commercial precursors. One approach is shown in Scheme VI. In the first step, organozinc reagent 33 obtained from 11-bromoundecyl acetate is coupled with p-iodobenzyl bromide 5 to produce 12-(p-iodophenyl)dodecyl acetate 34. Hydrolysis of the acetate 34 and conversion of 12-(p-iodophenyl)dodecanol 7 into iodide 35 provides a coupling partner for the next reaction with organozinc reagent 36. Final coupling product 37 is an ester which is converted into 18-(p-iodophenyl)octadecanol 12 in a two-steps process. In a summary, the chain elongation process can be abbreviated as $IPhC_1+C_{11}+C_6=IPhC_{18}$.

Scheme VI:

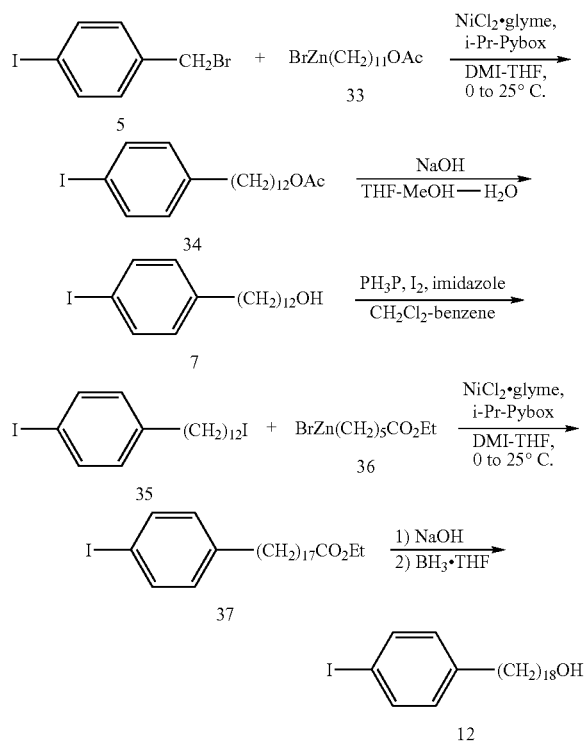

Methods

Synthesis of 12-(p-Iodophenyl)dodecyl acetate (34)

Zinc powder (146 mg, 2.25 mmol) was heated to 70° C. in a 10-ml Schlenk tube under high vacuum for 30 min. After back-filling with nitrogen, DMA (2 ml) and iodine (19 mg, 0.08 mmol) were added, and the resulting mixture was stirred until the color of iodine had faded. Then, neat 11-bromoundecyl acetate (440 mg, 1.5 mmol) was added. The reaction mixture was stirred for 12 h at 70° C., cooled to the room temperature, excess of zinc was allowed to settle, and clear gray-colored solution of organozinc reagent was transferred into a 5-ml round bottom flask via cannula.

In a 10-ml flask, $NiCl_2$.glyme (40 mg, 0.18 mmol) and (R)-(i-Pr)-Pybox (or (S)-(i-Pr)-Pybox) (68 mg, 0.225 mmol) were dissolved in DMA (1.5 ml) and solution of p-iodobenzyl bromide 5 in THF (0.7 ml) was added. After stirring for 10 min at 0° C. for 10 min, organozinc reagent 33 was added. Reaction mixture was stirred at 0° C. for 30 min and at room temperature for 12 h. Reaction mixture was quenched with $NH_4Cl$ solution, extracted with EtOAc, extract was dried over $Na_2SO_4$ and evaporated. Residue was chromatographed on silica gel in hexane-ether (98:2) to give the product, 408 mg (63%).

Using catalyst composed of $Ni(COD)_2$ (0.05 eq) and (i-Pr)-Pybox (0.1 eq) in this procedure resulted in 72% yield.

Synthesis of 12-(β-Iodophenyl)dodecanol (7)

12-(p-Iodophenyl)dodecyl acetate 34 (872 mg, 2.03 mol) was dissolved in THF (4 ml) and MeOH (4 ml) mixture, and a solution of NaOH (325 mg, 8.11 mmol) in $H_2O$ (1 ml) was added. Reaction mixture was stirred at room temperature for 5 h, quenched with 1 N HCl to pH 7, diluted with $NaHCO_3$ solution and extracted with EtOAc. Extract was dried over dried over $Na_2SO_4$ and the solvent was evaporated. Silica gel chromatography of the residue in hexane-ethyl acetate (95:5, 90:10) gave the product (682 mg, 87%) as a white solid.

Synthesis of 12-(p-Iodophenyl)dodecyl iodide (35)

12-(p-Iodophenyl)dodecanol 7 (676 mg, 1.74 mmol), $Ph_3P$ (548 mg, 2.09 mmol) and imidazole (196 mg, 2.87 mmol) were dissolved in the mixture of $CH_2Cl_2$ (8 ml) and benzene (5 ml) and cooled to 0° C. Solid $I_2$ (530 mg, 2.09 mmol) was added. Reaction mixture was stirred at 0° C. for 30 min, and at room temperature for 1 h. Reaction was quenched by the addition of MeOH (1 ml), diluted with $NaHCO_3$ solution and extracted with EtOAc. Chromatography in hexane-$CH_2Cl_2$ (98:2) gave the product as a white solid, 802 mg (93%).

Synthesis of Ethyl 18-(p-iodophenyl)octadecanoate (37) from (35)

Zinc powder (156 mg, 2.4 mmol) was heated to 70° C. in a 10-ml Schlenk tube under high vacuum for 30 min. After back-filling with nitrogen, DMA (1.5 ml) and iodine (20 mg, 0.08 mmol) were added. After the color of iodine had disappeared, neat ethyl 6-bromohexanoate (0.29 ml, 1.61 mmol) was added. Reaction mixture was stirred at 70° C. for 10 h, cooled to the room temperature, zinc excess was allowed to settle, and the organozinc solution was transferred via cannula into a storage vessel. In a 10-ml flask, $NiCl_2$.glyme (18 mg, 0.08 mmol) and (R)-(i-Pr)-Pybox (or (S)-(i-Pr)-Pybox) (31 mg, 0.1 mmol) were dissolved in DMA (2.5 ml) and THF (0.5 ml), cooled to 0° C. and solution of organozinc reagent 36 was added via cannula. Reaction mixture was stirred at 0° C. for 10 h and at room temperature for 24 h, then quenched with $NH_4Cl$ solution and extracted with EtOAc. The organic extract was dried over $Na_2SO_4$ and evaporated. The crude product was purified by silica gel chromatography in hexane-ether (98:2, 97:3) to give the product, 281 mg (68%).

Using catalyst composed of $Ni(COD)_2$ (0.04 eq) and (s-Bu)-Pybox (0.08 eq) and DMA as a solvent in this procedure resulted in 36% yield.

Synthesis of 18-(p-Iodophenyl)octadecanol (12) from (37)

Ethyl 18-(p-iodophenyl)octadecanoate 37 (270 mg, 0.52 mmol) was dissolved in THF (3 ml) and MeOH (3 ml) mixture, and solution of NaOH (300 mg, 7.5 mmol) in $H_2O$ (0.7 ml) was added. Reaction mixture was stirred at room temperature for 4 h, quenched with 8 ml of 1 N HCl and extracted with EtOAc. Organic extract was washed with NaCl solution twice, dried over $Na_2SO_4$ and evaporated to give 254 mg of the crude material.

Crude material was dissolved in THF (1 ml) and $BH_3$.THF (3 ml, 3 mmol) was added at 0° C. Reaction mixture was kept in a refrigerator at +4° C. overnight, and then quenched with $H_2O$ at 0° C. Mixture was extracted with EtOAc, extract was dried over $Na_2SO_4$ and evaporated. Residue was purified by silica gel chromatography in hexane-EtOAc (95:5, 90:10) to give the product, 232 mg (94%).

Another possibility based on different cross-coupling partners is shown in Scheme VII. The chain elongation sequence is $C_6+C_{11}+IPhC_1=IPhC_{18}$. First coupling between THP ether of 6-iodohexanol 38 and $C_{11}$ organozinc reagent 33 produces $C_{17}$ fragment 39. Removal of THP protecting group, conversion of intermediate alcohol into bromide 40 followed by formation of organozinc 41 produces another partner for cross-coupling reaction. Ni(II)-catalyzed coupling of organozinc 41 with p-iodobenzyl bromide 5 completes the chain elongation. Hydrolysis of acetate 42 gives 18-(p-iodophenyl)octadecanol 12.

Scheme VII:

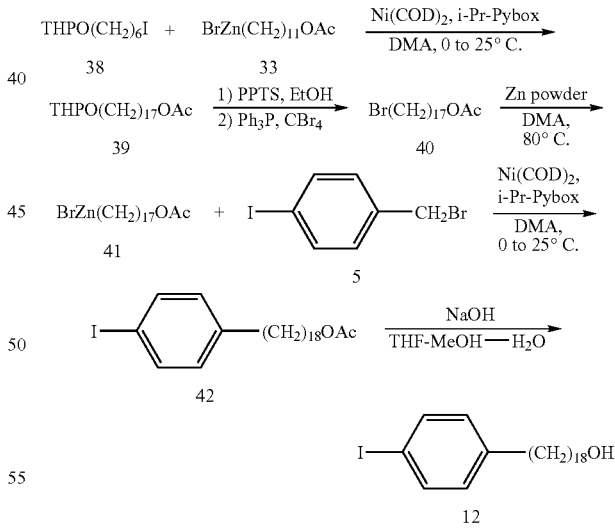

Synthesis of Tetrahydro-2-(17-acetoxyheptadecyloxy)-2H-pyran (39)

In a 10-ml Schlenk tube, zinc powder (98 mg, 1.5 mmol) was dried at 70° C. under high vacuum for 30 min. After back-filling with nitrogen, DMI (1 ml) and iodine (13 mg, 0.05 mmol) were added. The mixture was stirred until disappearance of the iodine color, after which neat 11-bromoundecyl acetate (293 mg, 1 mmol) was added. The tube was sealed, and the mixture was stirred at 70° C. for 12 h, cooled to the room temperature and zinc excess was allowed to settle. In a 5-ml flask, $NiCl_2$.glyme (17 mg, 0.08 mmol) and (R)-(i-Pr)-Pybox (or (S)-(i-Pr)-Pybox) (30 mg, 0.1 mmol) were dissolved in DMI (1 ml) and THF (0.3 ml), then neat $I(CH_2)_6$OTHP 38 (240 mg, 0.77 mmol) was added followed by addition of the organozinc solution 33 via cannula. Reaction mixture was stirred at room temperature for 14 h, quenched with $NH_4Cl$ and extracted with EtOAc. Extract was dried over $Na_2SO_4$ and concentrated by solvent evaporation. Chromatography in hexane-ethyl ether (15:1, 10:1) gave the product, 212 mg (69%).

Synthesis of 17-Acetoxy-heptadecyl bromide (40)

THP ether 39 (1.207 g, 3.03 mmol) was dissolved in 95% EtOH (12 ml) and PPTS (76 mg, 0.3 mmol) was added. Reaction mixture was stirred at 55° C. for 4 h, cooled to room temperature and diluted with EtOAc. Mixture was washed with $H_2O$ three times, organic extract was dried over $Na_2SO_4$ and evaporated. Residue was chromatographed on silica gel to give 864 mg (91%) of 17-acetoxy-heptadecanol.

Synthesis of 18-(p-Iodophenyl)octadecyl acetate (42)

Zinc powder (340 mg, 5.21 mmol) was dried in a 25-ml flask under high vacuum at 70° C. for 30 min, then DMA (1 ml) and 12 (44 mg, 0.17 mmol) were added. After 10 min, solution or 17-acetoxy-heptadecyl iodide (1.473 g, 3.47 mmol) in DMA (5 ml) was added. Reaction mixture was stirred at 60-70° C. for 10 h, cooled to room temperature and solution of the organozinc reagent was transferred via cannula into 25 ml round bottom flask equipped with the stir bar. The flask with organozinc solution 41 was immersed into an ice bath. In a 10-ml round bottom flask, $NiCl_2$.glyme (76 mg, 0.347 mmol) and (R)-(i-Pr)-Pybox (or (S)-(i-Pr)-Pybox) (136 mg, 0.45 mmol) were dissolved in DMA (2 ml), then solution of p-iodobenzyl bromide (1.55 g, 5.21 mmol) in DMA (3 ml) was added. The solution of $NiCl_2$-Pybox catalyst and p-iodobenzyl bromide was added to the solution of organozinc reagent 41 at 0° C. within 2-3 min. Reaction mixture was stirred at 0° C. for 30 min and at room temperature for 12-24 h. The reaction was quenched by addition of aqueous $NH_4Cl$, extracted with EtOAc, extract was dried over $Na_2SO_4$ and evaporated. The crude product was purified by silica gel chromatography in hexane-ether (98:2) to give the product (1.58 g, 88%).

Synthesis of 18-(p-Iodophenyl)octadecanol (12) from (42)

18-(p-Iodophenyl)octadecyl acetate 42 (1.55 g, 3.01 mmol) was dissolved in THF (10 ml), MeOH (5 ml) and solution of NaOH (240 mg, 6.03 mmol) in $H_2O$ (1 ml) was added. The reaction mixture was stirred at room temperature for 2 h, quenched with aqueous $NaHCO_3$ solution and extracted with EtOAc. Extract was dried over $Na_2SO_4$ and evaporated. Silica gel chromatography in hexane-EtOAc (95:5, 90:10) gave the product, 1.36 g (95%).

In general, the choice of coupling partners may depend on commercial availability of starting materials since the $C_{18}$ alkyl chain can be assembled from many different fragments (more than two or three). In addition to alkyl bromides, alkyl iodides can be used for generation of organozinc reagents. p-Iodobenzyl chloride can be used instead of p-iodobenzyl bromide 5. As described by G. Fu, $Ni(COD)_2$, $NiCl_2$.glyme or $NiBr_2$.diglyme can be used as Ni(II) sources, and compounds 71, 72, 73 or 74 in any enantiomeric form can serve as ligands (Zhou J R, Fu G C. J. Am. Chem. Soc. 2003; 125: 14726-14727; Fischer C, Fu G C. J. Am. Chem. Soc. 2005; 127: 4594-4595; Arp F O, Fu G C. J. Am. Chem. Soc. 2005; 127: 10482-10483). N,N-Dimethylacetamide (DMA), N-methyl-2-pyrrolidone (NMP) or 1,3-dimethyl-2-imidazolidinone (DMI) in combination with THF can be used as solvents for cross-coupling reaction.

Another approach is shown in Scheme VIII. It can be described as $C_{16}+IPhC_2=IPhC_{18}$. The $C_{16}$ fragment 43 originates from relatively inexpensive 16-hexadecanolactone 31. Lactone cleavage with trimethylsilyl iodide in the presence of ethanol results in ethyl 16-iodohexadecanoate 43. Iodoester 43 is coupled with organozinc reagent 44 made from 2-(p-iodophenyl)ethyl bromide to give ester 37 which has the 18 carbon chain required for NM404. Ester 37 is converted into 18-(p-iodophenyl)octadecanol 12 in two steps as shown in Scheme VIII.

Scheme VIII:

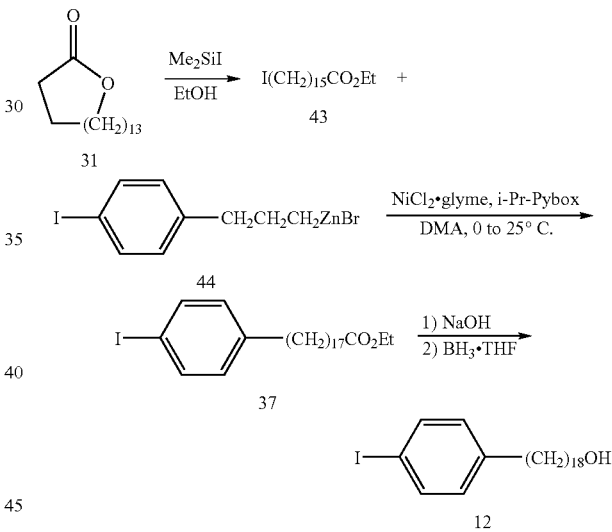

Synthesis of 43 is based on procedures well-known in the art. See, for example, Canadian Patent No. CA 2 339 495.

Conversion of 18-(p-iodophenyl)octadecanol 12 into 18-(p-iodophenyl)-octadecyl phosphocholine 1 (NM404) is performed by the procedure used by the inventors (Pinchuk A N, Rampy M A, Longino L A, Skinner R W S, Gross M D, Weichert J P, Counsell R E. J. Med. Chem. 2006; 49: 2155-2165) (Scheme IX).

Scheme IX:

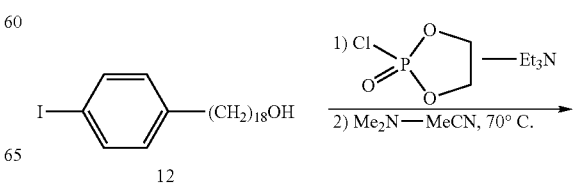

-continued

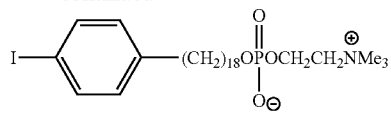

1

Synthesis of PLE Boronic Ester

While the above recited synthesis has been used to produce radiolabeled PLE compounds, similar synthesis schemes can be used to produce boron esters of PLEs. These boronic esters have the general structure:

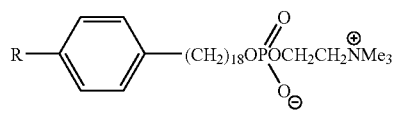

45 where R is:

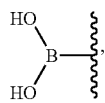

46

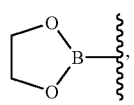

47

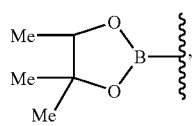

48

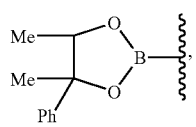

49

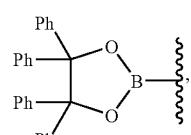

50

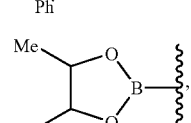

51

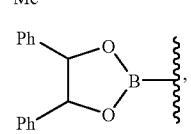

52

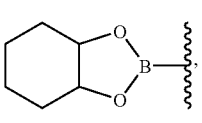

53

-continued

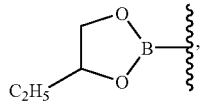

54

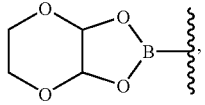

55

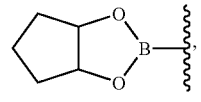

56

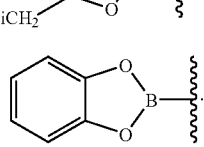

57 and

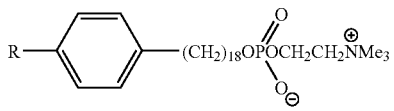

58

Compounds 46-57 are boronic esters of the following 1,2-diols: pinacol, ethylene glycol; 2,3-diphenyl-butane-2,3-diol; butane-1,2-diol; catechol; 1,1,2,2-tetraphenyl-1,2-ethanediol; butane-2,3-diol; 2,3-diphenyl-2,3-butanediol; cis- and trans-cyclohexane-1,2-diol; trans-1,4-dioxane-2,3-diol; cis- and trans-cyclopentane-1,2-diol and 3-(trimethylsilyl)-propane-1,2-diol.

Other boronic esters of the phospholipid compounds disclosed herein have the structure:

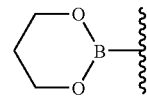

45 where R is:

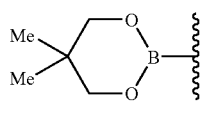

58

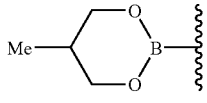

59

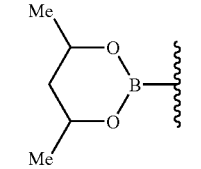

60

61

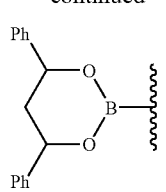 62

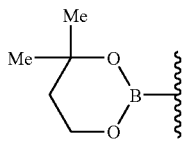 63

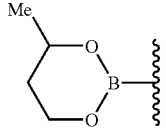 64

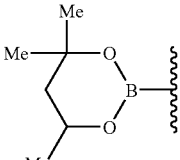 65

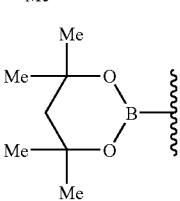 66

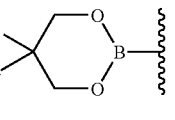 67 and

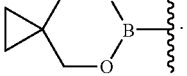 68

These compounds, 58-68, are boronic esters of the following 1,3-diols: propane-1,3-diol; 2,2-dimethyl-propane-1,3-diol; 2-methyl-propane-1,3-diol; pentane-2,4-diol; 1,3-diphenyl-propane-1,3-diol; 3-methyl-butane-1,3-diol; butane-1,3-diol; 2-methyl-pentane-2,4-diol; 2,4-dimethyl-pentane-2,4-diol; 2-methyl-2-propyl-propane-1,3-diol and 1,1-bis-(hydroxymethyl)cyclopropane.

Additionally, boron intermediates for radioiodination, organotrifluoroborate intermediate include:

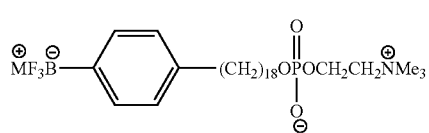 70 where M is selected from the group consisting of Li, Na, K, Cs and Rb. Such compounds have previously been described by Kabalka, U.S. Pat. No. 7,041,859. However, while Kabalka teaches the general use of trifluoroborates as intermediates in the synthesis of halogenated organic compounds, he does not teach the use of 70, above, or the use of trifluoroborates, in general, for the synthesis of boronic esters.

Additional oxidants to be used for radioiodination may include: dichloramine-T; chloramine-B, dichloramine-B; iodogen, iodogen coated tubes, iodobeads, N-chlorosuccinimide; hydrogen peroxide, peracetic acid, m-chloro-perbenzoic acid and peroxidase.

Tumor Selectivity of PLE Analogs

Biology

The avidity of PLE and APC analogs to localize in tumors was evaluated in several animal models. The PC-3 model represents a human tumor cell line that was used to determine the target (tumor) to non-target ratio of NM404 and NM412 in head to head comparison in order to select a candidate for an initial human pharmacokinetic trial in prostate cancer patients. The MatLyLu (Dunning R3327 rat) model, a rat prostate tumor line, was used specifically to screen 9 specific analogs prior to entering them into control for dosimetry and tumor-bearing animals for determining tumor/background ratios. Finally, the Walker-256 carcinosarcoma model was used for quantitative tissue distribution purposes.

In order to expedite the screening process and minimize the number of tumor bearing animals utilized in multiple time point tissue distribution studies, new radioiodinated homologs were imaged by gamma camera scintigraphy in the rat Dunning R3337 (MAT LyLu strain) prostate cancer model. Thus, male Copenhagen rats received a subcutaneous injection of MAT LyLu cells ($1\times10^6$ cells) in the thigh 10-14 days prior to injection of the radioiodinated PLE analogs (30-40 µCi) in 2% Tween-20 solution. Gamma camera images were obtained at multiple time points including 24 and 48 hours post injection. Homologs (NM410, NM413, and NM414) displaying high hepatic uptake, significant abdominal accumulation and retention or poor tumor uptake and retention were not submitted to subsequent biodistribution analysis. Tissue distribution of radioactivity in rats bearing Walker-256 carcinosarcoma was assessed at various time intervals following intravenous administration of the radioiodinated chain length homologs. The first group of compounds that was tested included three alkylphosphocholines: a shorter chain analog with seven carbons NM396 and two analogs with a longer chain length, 13 (NM397, C15 alkyl chain length) and 1 (NM404, C18 alkyl chain length).

Initial biodistribution experiments performed with NM396 (C7 analog) indicated rapid tissue clearance accompanied by significant in vivo deiodination. By 24 hours, the amount of radioactivity in the thyroid was 213% ID/g, whereas levels of radioactivity in all of the organs surveyed was <0.10% ID/g. Reducing the number of methylene groups to seven apparently afforded a much more hydrophilic molecule which was rapidly excreted by the kidneys. In contrast to compound NM346 (C12 analog), the C7 analog NM396 cleared rapidly from the rat and did not localize in tumor tissue at any of the time points examined.

The tissue distribution of the C15 homolog 13 (NM397) was assessed utilizing the same Walker 256 rat tumor model. Radioactivity in the tumor increased with time and peaked at 48 hours after administration (1.65±0.23% of ID/g) as opposed to most normal tissues which exhibited their highest levels of radioactivity 6 hours after administration. With the exception of thyroid, the tumor had higher radioactivity concentrations at 24, 48, and 120 hours than any of the other tissues surveyed. A more rapid washout of radioactivity occurred in the normal tissues as compared to the tumor presumably due to metabolism and elimination by normal tissues. The accumulation of radioactivity in the thyroid increased throughout the course of the study suggesting the presence of a low level of in vivo deiodination. Levels of radioactivity in the duodenum were similar to those of tumor with maximum levels being observed at 48 hours after administration (1.38±0.24% ID/g).

Although limited results were obtained with the C12 analog NM346 in this model, results suggest that the tissue distribution profile of the C15 analog 13 (NM397) was similar to that observed with the C12 analog NM346 with the exception of a 2-fold increase in tumor uptake at 24 h. Remaining uptake and clearance in other organs and tissues was similar between the two compounds.

The effect of further extending the aliphatic chain to the C18 analog 1 (NM404) depicted a dynamic profile of this compound that was similar to the C15 analog 13 (NM397) as levels of radioactivity peaked in the tumor 48 hours after administration (1.14±0.01% of ID/g), albeit at slightly lower levels. Quantities of radioactivity detected in liver, kidney and duodenum were significantly lower following administration of the C18 compound 1 as compared to the same organs in the C15 analog 13 studies. In addition, the C18 analog 1 was retained in the circulation to a much greater extent than the other chain length homologs surveyed. For example, at 120 hours, blood levels for 1 were 0.6±0.1% of ID/g as compared to levels of 0.07±0.00% of ID/g for the C15 (13) analog. Total radioactivity levels in the thyroid were relatively low in both 13 and 1 when the extremely small mass of the gland is considered.

In order to examine the transport properties of PLE analogs, plasma was isolated from Walker-256 tumor-bearing rats 7 days after administration of iodine-125 labeled 1. The distribution of radioactivity in the plasma compartment of a rat receiving 1 (NM404) was studied. PAGE analysis revealed that most of the circulating radioactivity (88%) was associated with the albumin fraction following administration of the C18 analog 1. This finding is similar to results reported by Eibl who studied binding of phospholipid ether prototype, ET-18-OCH$_3$, with serum proteins and found that the majority of the ether lipid (71%) was bound to albumin and about 6% to HDL (Kötting J, Marschner N W, Neumüller W, Unger C, Eibl H. Hexadecylphosphocholine and octadecyl-methyl-glycero-3-phosphocholine: a comparison of hemolytic activity, serum binding and tissue distribution. In: *Progress in Experimental Tumor Research*; Eibl H, Hilgard P, Unger C. Eds.; Karger: Basel, Switzerland, 1992, 34, pp 131-142).

Comparative Imaging Studies

Figure 5:
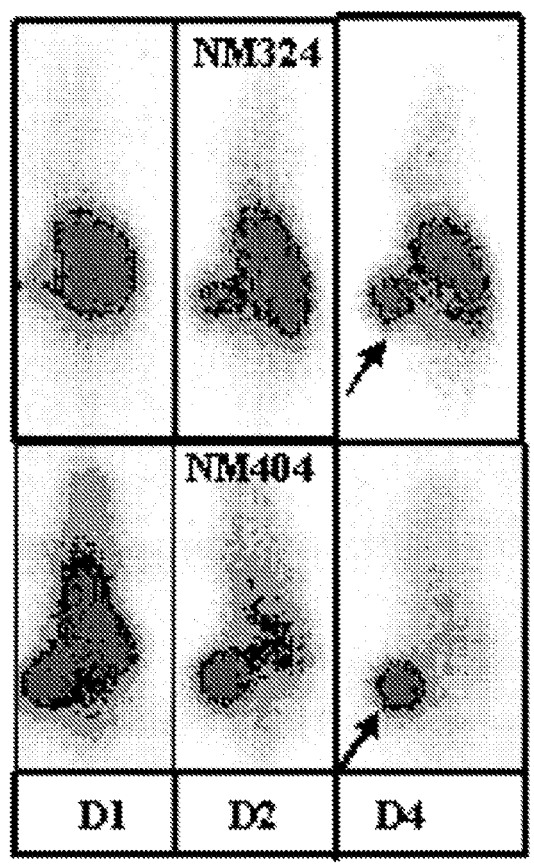
FIG. 5 is a scintigraphic comparison of NM404 (bottom panel) and NM324 (top panel) at 1, 2, and 4 days in a SCID mouse with human prostate PC-3 tumor (arrow) implanted in the flank. Liver and background radioactivity are much improved with NM404.

Gamma camera scintigraphy images shown in FIG. 5 directly compare the tumor uptake and body clearance of second generation analog $^{125}$I-NM404 (1) versus its shorter chain, first generation predecessor, $^{125}$I-NM324 (12-(m-iodophenyl)dodecyl phosphocholine) at 1, 2, and 4 days post administration in immune-compromised SCID mice bearing human PC-3 prostate tumor xenografts. Qualitative scintigraphic comparison of these two PLE analogs demonstrated a striking difference in tumor uptake and overall body clearance. The longer chain agent, NM404, displays rapid tumor uptake and prolonged retention accompanied by rapid whole body elimination of radioactivity, whereas tumor uptake and body clearance are substantially delayed with NM324, even at 4 days following administration. Significant tumor uptake and retention of C18 analog NM404 accompanied by rapid whole body elimination clearly defined the superior imaging properties of NM404 in this model.

Extensive quantitative tissue distribution results obtained at 1, 3, 5, and 8 days following administration of radioiodinated NM404 in this model indicated rapid elimination of radioactivity from all normal tissues over the 8 day evaluation period. Tumor uptake, however, continued to increase up until day 5 when it reached 18% injected dose per gram of tumor. Tumor to background tissue ratios steadily increased over the course of the experiment due to prolonged retention in tumors coupled with a steady elimination from normal tissues. Tumor to background tissue ratios exceeded 4, 6.8, 23, and 9 in blood, liver, muscle, and prostate, respectively, 3 days after injection and continued to improve at 5 and 8 days. Again, although thyroid levels ranged from 26 to 54% injected dose per gram of tissue, these levels are actually quite low and represent an extremely small percentage of the injected dose when the exceedingly small mass of the organ is considered and the data are presented on a percent administered dose per organ basis.

Tumors were readily visualized with the C12 (NM346), C15 (NM347) and C18 (NM404) alkyl phosphocholine homologs via gamma camera scintigraphy at both 24 and 48 hours after injection. Rat imaging results obtained with C15 (26, NM413) and C18 (27, NM412) propanediol analogs, on the other hand, displayed tumor uptake accompanied by high liver and abdominal radioactivity levels. Imaging results obtained with C15 (28, NM414) and C18 (29, NM410) 2-O-Me glycerol analogs in the MAT LyLu prostate model indicated high radioactivity levels in the liver and abdomen with little to no uptake of the agent into tumors.

Qualitative rat whole body screening scans acquired in MAT-LyLu tumor bearing rats with radioiodinated PLE analogs with longer chain lengths revealed sufficient tumor uptake to permit detection. However, follow-up tissue distribution studies have shown that sequential increases in the chain length from C12 to C15 to C18, resulted in a rapid decline in the amount of radioactivity detected in the non-target organs. This substantial decrease in non-target tissue activity was accompanied by a relatively small reduction in the levels of radioactivity present in the tumor. In addition, the C18 analog 1 (NM404) displayed a propensity to remain in the circulation much longer than the C12 (NM346) and C15 (13, NM397) analogs. A longer plasma half-life is expected to result in additional opportunities for uptake of the C18 compound 1 by the tumor as it continually circulates through the vasculature. This extended plasma half-life may be a result of strong binding of the probe to albumin. Uptake and transport of labeled PLE by plasma components may also be an important factor related to the tumor retention of these compounds. Certainly, increase of the chain length from C7 to C18, results in an increase in the lipophilicity of the PLE and APC analogs. Greater lipophilicity may increase the affinity of these compounds for the cell membrane, and may alter their binding to plasma components. Uptake and transport in the circulation by endogenous lipoproteins such as LDL and HDL may also impact the biological distribution into the tumor.

Figure 6:
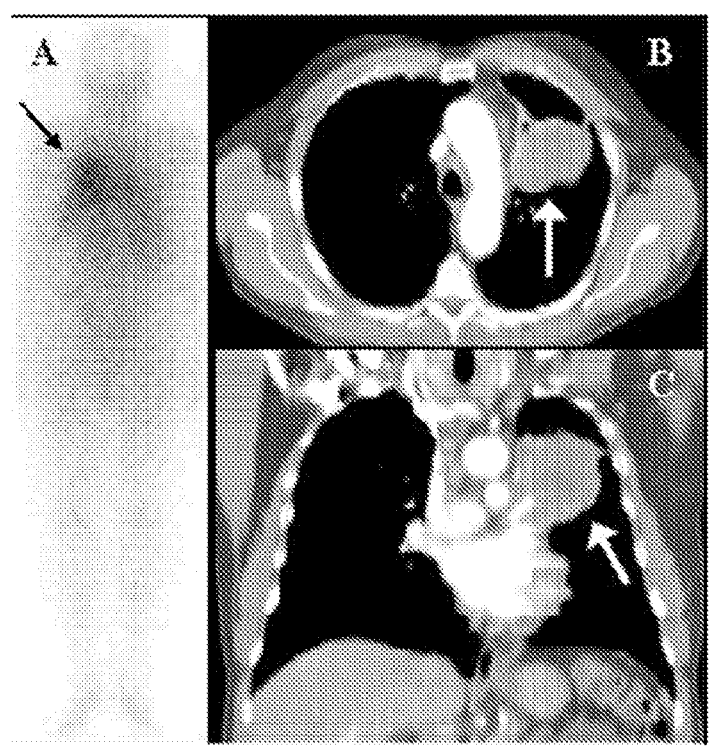
FIG. 6A-C images of lung cancer patient, posterior whole body planar nuclear medicine image (A) 4 days after iv administration of $^{131}$I-NM404 (0.8 mCi) to a patient with non small cell lung cancer (6 cm dia., arrow). Lung tumor is easily detected in corresponding axial (B) and coronal (C) computed tomography (CT) scans.

In preparation for human clinical trials, unlabeled NM404 was subjected to independent (University of Buffalo Toxicology Research Center) acute toxicity evaluation at 1200 times the anticipated imaging mass dose in rats and rabbits. The agent was well tolerated and no acute toxicities were found at this dose level. Due to its selective tumor uptake and retention properties in a variety of rodent tumor models and subsequent excellent safety profile in rats and rabbits, NM404 was selected to undergo initial human pharmacokinetic evaluation in non-small cell lung cancer (NSCLC) patients. Patients underwent planar gamma-camera scintigraphy after receiving an injection of $^{131}$I-NM404 (<1 mCi). Preliminary human results (n=3) demonstrated tumor uptake and prolonged retention in primary lung tumors (FIG. 6). Relative to the high liver uptake values observed with its predecessor, NM324, however, liver and abdominal radioactivity levels were much lower with NM404, suggesting the feasibility of evaluating this agent in other abdominal tumors including those associated with the colon, prostate, and pancreas.

Figure 7:
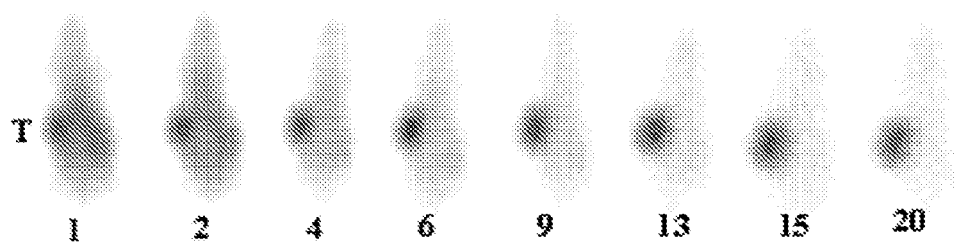
FIG. 7 shows images of time course (days) in a SCID mouse with a human RL-251 adrenal tumor (T) xenograft after dosing NM404 at day 1.
Figure 8:
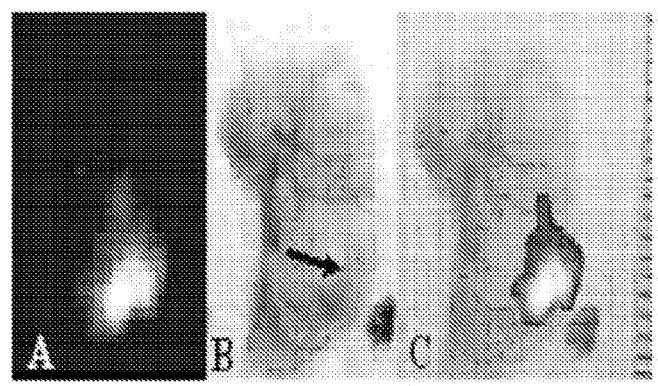
FIG. 8A-C shows images obtained using $^{125}$I-NM404 to label tumor.

NM404 has now been evaluated in 27 animal tumor models, including several lung models, and it is clear that once the agent enters tumor cells, it reaches a metabolic dead end and becomes trapped. Prolonged tumor retention of this agent is demonstrated in a human adrenal tumor xenograft implanted into SCID mice (FIG. 7). NM404 is also retained in spontaneous murine lung tumors (FIG. 8). Using $^{125}$I-labeled NM404, the inventors have been able to image mammary and prostate tumors in mice in excess of 60 days. Prolonged tumor retention characteristics may significantly enhance the radiotherapeutic efficacy of the agent. Imaging and tissue distribution studies performed in mouse models aimed at determining the uptake characteristics in a wide variety of tumor models are summarized in Table 1, below.

TABLE 1

Summary of Tumor Models examined with NM404
Table 1: Summary of Tumor Models

| Tumor Model | Species | Category | Uptake |
|---|---|---|---|
| Human Tumor Xenografts | | | |
| Prostate PC-3 | SCID Mouse | Adenocarcinoma | Yes |
| Lung A-549 (NSCLC) | SCID Mouse | Adenocarcinoma | Yes |
| Lung NCI H-69 (Oat Cell) | Nude Mouse | Adenocarcinoma | Yes |
| Adrenal H-295 | SCID Mouse | Adenocarcinoma | Yes |
| Adrenal RL-251 | SCID Mouse | Adenocarcinoma | Yes |
| Melanoma A-375 | Nude Mouse | Adenocarcinoma | Yes |
| Colon LS-180 | Nude Mouse | Adenocarcinoma | Yes |
| Ovarian HTB-77 | Nude Mouse | Adenocarcinoma | Yes |
| Animal Tumor Xenografts | | | |
| Mammary MCF-7 | Rat | Adenocarcinoma | Yes |
| Prostate MatLyLu | Rat | Adenocarcinoma | Yes |
| Walker-256 | Rat | Carcinosarcoma | Yes |
| Recent Rodent Models | | | |
| TRAMP prostate | Spontaneous mouse | Adenocarcinoma | Yes |
| Liver CT-26 | Mouse xenograft | Colorectal adenocarcinoma | Yes |
| Subcutaneous CT-26 | Mouse xenograft | Colorectal adenocarcinoma | Yes |
| Min Mouse Intestinal | Endogenous Mouse | Adenocarcinoma | Yes |
| Melanoma | Mouse xenograft | Adenocarcinoma | Yes |
| SCC1 and 6 | Nude mouse | Squamous cell carcinoma | Yes |
| Mammary SCC and ACC | Apc$^{Min/+}$mouse | Squamous cell carcinoma and Adenocarcinoma | Yes |
| Hepatocellular Carcinoma | Spontaneous TGF-α mouse | Adenocarcinoma | Yes |
| Pancreatic c-myc and kras | Spontaneous mice | Adenocarcinoma | Yes |
| Glioma L9 | Rat | Glioma | Yes |
| Retinoblastoma | Spontaneous Mouse | Blastoma | Yes |
| Cervical | Spontaneous Mouse | Adenocarcinoma | Yes |
| Adenomatous Polyp | Spontaneous Mouse | Adenoma | No |
| Mammary Hyperplasia | Endogenous Mouse | Alveolar Hyperplasia | No |

Successful Radiolabeling of NM404 with Iodine-124

The inventors have obtained high specific activity sodium iodide-124 in 0.1N NaOH (Eastern Isotopes, Sterling, Va.). Radiolabeling of NM404 is achieved in greater than 60% isolated radiochemical yield by modification of an isotope exchange method. Briefly, a 2-ml glass vial is charged with 10 mg of ammonium sulfate dissolved in 50 l of deionized water. Glass beads are added, a Teflon lined septum and screw cap are added and the vial gently swirled. A solution of 10 μg (in 10 μl of ethanol) of stock NM404 is added followed by aqueous sodium iodide-124 (1-5 mCi) in less than 30 μl aqueous 0.01 N sodium hydroxide. The reaction vile is swirled gently. A 5-ml disposable syringe containing glass wool in tandem with another 5-ml charcoal nugget filled syringe with needle outlet are attached. The glass wool syringe acts as a condensation chamber to catch evaporating solvents and the charcoal syringe traps free iodide/iodine. The reaction vessel is heated in a heating block apparatus for 45 minutes at 150° C. after which four 20 ml volumes of air are injected into the reaction vial with a 25-ml disposable syringe and allowed to vent through the dual trap attachment. The temperature is raised to 160° C. and the reaction vial is heated another 30 minutes. After cooling to room temperature, ethanol (200 μl) is added and the vial swirled. The ethanolic solution is passed through a pre-equilibrated Amberlite IRA 400-OH resin column to remove unreacted iodide. The eluate volume is reduced to 50 μl via a nitrogen stream (use charcoal syringe trap) and the remaining volume injected onto a silica gel column (Perkin Elmer, 3 μm×3 cm disposable cartridge column eluted at 1 ml/min with hexane/isopropanol/water (52:40:8)) for purification. Final purity is determined by TLC (plastic backed silica gel-60 eluted with chloroform-methanol-water (65:35:4, $R_f$=0.1). The HPLC solvents are removed by rotary evaporation and the resulting radioiodinated NM404 is solubilized in aqueous 2% Polysorbate-20 and passed through a 0.22 μm filter into a sterile vial. Radiochemical purity is typically greater than 99%.

Toxicology

The inventors have previously performed various studies investigating the toxicity of the PLE analogs described herein. As outlined below and as described in-depth in, for example, U.S. patent application Ser. Nos. 10/906,687, 11/177,749 and 11/316,645, the PLE analogs described herein show little or no toxicity. Further, boron compounds, such as those conventionally used for BNCT, have been found to have similar toxicity to common sodium chloride. In cases of excess boron ingestion, studies have shown that boric acid is excreted rapidly in the urine and disappears within 4 days. Thus, the boron esters of the PLE compounds described herein should provide the ideal combination of physiologic nontoxicity and cancer specificity.

Toxicology Studies Performed for NM404

| Report/Study No. | Administration | Animals | Observation Period | GLP |
|---|---|---|---|---|
| Study 27 | Single Dose | Male Rats | 14 Days | Yes |
| Study 28 | Single Dose | Male Rabbits | 14 Days | Yes |
| Study 31 | Single Dose | Female Rats | 14 Days | Yes |
| Study 32 | Single Dose | Female Rabbits | 14 Days | Yes |

Formal toxicology studies of NM404 in male rats and rabbits were performed at the Toxicology Research Center of the State University of New York at Buffalo under the direction of Dr. Paul Kostyniak. Drug vehicle and drug product were provided to Dr. Kostyniak by Dr. Raymond Counsell of the University of Michigan for testing as described in the appended synopses of Study 27 and Study 28. No significant toxic effects were noted at a dose of 4 mg/kg, which is a dose approximately 200 times the anticipated imaging dose at that time, and the inventors estimate to be approximately 2860 times the anticipated therapy dose for clinical trials under this invention. Human safety studies of unlabeled NM404 were initiated in normal male humans at a mass of 10 times the anticipated imaging dose and about 21 times the anticipated therapy dose. The results again showed no toxicity attributable to the drug substance. This toxicology study was performed under GLP conditions.

Subsequently, the inventors initiated a toxicology study of unlabeled NM404 in female rats and rabbits (Study 31 and Study 32) at the Toxicology Research Center at SUNY-Buffalo in order to expand the patient population to be studied in the NSCLC Phase 1 clinical trial. No significant toxic effects were noted at a dose of 0.04 mg/kg, a dose approximately 200 times the revised imaging mass dose, estimated to be approximately 286 times the anticipated therapy dose for clinical trials. Human safety studies of unlabeled NM404 were initiated in normal female humans at a mass of 10 times the initially anticipated imaging dose and about 21 times the anticipated therapy dose. Again, no significant toxic effects were noted in either female rats or rabbits. This toxicology study was performed under GLP conditions.

Preclinical Pharmacology

Extensive structure activity relationship studies resulted in the synthesis, radiolabeling, and evaluation of over 20 phospholipid ether analogs as potential tumor-selective imaging agents. The iodinated APC analogues were readily labeled with all iodine radioisotopes using an isotope exchange method (see above). These PLE analogs are specifically designed to incorporate aromatic radioiodine in order to render the molecule stable towards in vivo deiodination. The low level of thyroid activity in all prior preclinical imaging and tissue distribution studies (on both a % injected dose/g and % injected dose/organ basis) has confirmed the in vivo stability of the PLE analogs.

Figure 9:
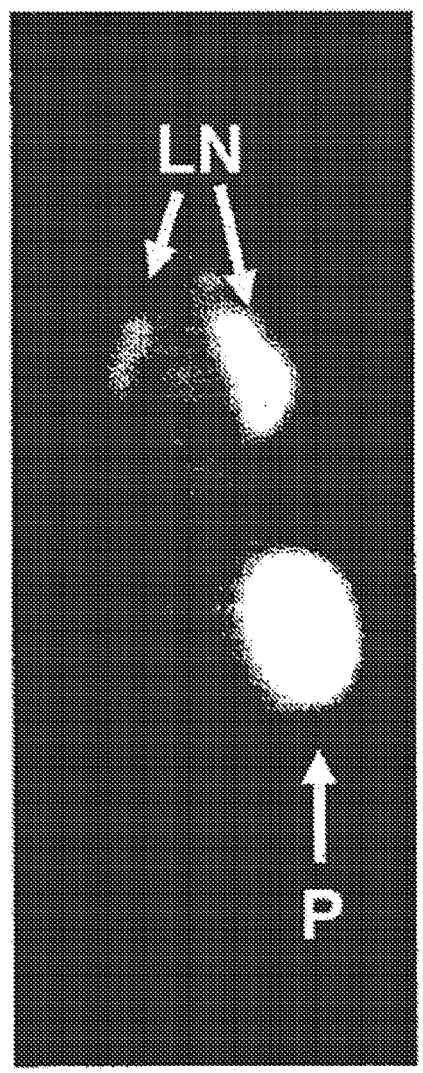
FIG. 9 shows a $^{124}$I-NM404 microPET scan of a SCID mouse with advanced metastatic human PC-3 prostate cancer. Image acquired 48 h post NM404 iv injection and shows significant uptake in both primary flank tumor xenograft (P) as well as in both axial lymph node (LN) and contralateral axial lymph node (LN). In this image the head is up and the tail is oriented down.

From the library of phospholipid ether (PLE) and alkyl phosphocholine (APC) compounds, NM324 [12-(3-iodophenyl)-dodecyl phosphocholine], initially showed the most promise in animal tumor localization studies. A variety of tumors including mammary, prostate, squamous cell carcinoma, ovarian, colorectal, and melanoma were successfully visualized by scintigraphy with NM324. During initial human pharmacokinetic studies with the prototype agent, NM324, an unacceptable accumulation in liver tissue was observed and additional experiments to identify PLE and APC compounds with superior tumor localization and background clearance properties were performed. Based upon this work, NM404 [18-(4-iodophenyl)-octadecyl phosphocholine] emerged due to its enhanced ability to localize in tumor, its increased metabolic clearance from the liver, and its longer plasma half-life. A key observation documented the ability of NM404 to localize in lymph node metastases, which were clearly delineated by scintigraphy in a metastatic prostate tumor model without retention in uninvolved lymph nodes, FIG. 9.

The lead compound NM404 has now been evaluated in over 27 animal tumor models and in every tumor model and tumor type studied so far, NM404 has shown tumor-selective retention. Prolonged tumor retention of $^{125}$I-NM404 has been demonstrated in mice for periods of 20-60 days post-injection. Such very extensive and protracted tumor retention, while significantly enhancing the radiotherapeutic efficacy of the agent, especially for isotopes with a slow radioactive decay like e.g. iodine-125 also enhances the efficiency of the agent when used for other radio therapies such as BNCT and external beam radiation since the PLE agent remains trapped in the neoplastic membrane.

Extensive biodistribution data for the prototype agent 125I-NM324 in several tumor models revealed tumor-to-blood ratios exceeding 8:1 at later post-injection times. In one such example in a rat mammary tumor model, tumor-to-normal tissue ratios reached a maximum at 96 hours with a tumor-to-blood ratio of 8.6 and tumor-to-muscle ratio of 20:1. Moreover, the heterogeneity of biodistribution of PLE-associated radioactivity within tumor was demonstrated by microautoradiography studies showing that the PLE radioactivity resides exclusively in viable tumor cells located toward the outer regions rather than the central necrotic regions. Comparative biodistribution data for NM324 and NM404 have been obtained in SCID mouse prostate and A549 lung cancer tumor models. These studies revealed high tumor-to-normal tissue ratios and tumor uptake exceeding 25% of the injected dose of NM404 within the tumor, thus supporting the desire to study the biodistribution of NM404 in humans.

Mechanism of Action

Formal metabolism studies were conducted on several PLE analogs including NM324, the predecessor of NM404. In these studies, each agent was examined to determine its ability to serve as substrates for enzymes associated with PLE metabolism. Three major enzymatic pathways are involved in the metabolism of PLE. O-Alkyl glycerol monooxygenase (AGMO) is responsible for cleavage of the alkyl ether linkage at C-1 to form either the long chain fatty alcohol or subsequently, the corresponding fatty acid. Phospholipases C (PLC) and D (PLD), on the other hand, give rise to the glycerol or phosphatidic acid products, respectively. Using a microsomal AGMO enzyme preparation, NM324 was not a substrate for this enzyme when compared to [$^3$H]-lyso-PAF (platelet activating factor), which was extensively metabolized. In a similar fashion, NM324 was analyzed as a substrate for PLC isolated from *Bacillus cereus* and was not hydrolyzed relative to 1-palmitoyl-2-[$^3$H]-palmitoyl-L-3-phosphatidylcholine (DPPC), which underwent significant hydrolysis.

Finally, several PLE analogs were subjected to a phospholipase D (PLD) assay. The PLD, which was isolated from cabbage, is similar to mammalian PLD in that the cabbage form affords phosphatidylethanol-type products in addition to phosphatidic acid when the enzymatic reaction is performed in the presence of ethanol. Several of the PLE analogs subjected to these assay conditions did give rise to the phosphatidylethanol adduct, indicating possible interaction with PLD. Without being held to any particular theory, one proposed mechanism is that PLEs are a metabolic substrate to human Phospholipase D, and that the relative absence of Phospholipase D in cancer cell membranes is the underlying mechanism for tumor-selective retention of PLEs such as NM404. Although known from the literature, it is still unclear why cancers lack PLD in their membranes.

Several NM404 precursors were also subjected to in vitro metabolism studies in various cell lines including Walker tumor cells, rat muscle (H9c2), and rat hepatocytes. In these studies, the extent of metabolism was determined on the basis of radiolabeled products formed after incubation for various time periods and the results normalized to cell number or the amount of cellular protein. Subsequent lipid extraction of the incubation medium and cell suspension demonstrated little generation of PLE metabolites in the Walker tumor cells whereas a significant production of metabolites was seen in both the muscle cells and hepatocytes over the 48 h time period studied. These results correlate well with in vivo biodistribution studies completed on all analogs. Although several studies have been completed, the role of metabolic trapping in the uptake and retention of radiolabeled PLE analogs in tumor cells is not well defined and currently remains an active area of examination. Without being held to any particular theory, the inventors believe that NM404 can enter the cell membranes of all cells, but gets eliminated from non-cancerous cells through rapid metabolism, whereas in cancer cells it gets trapped due to lack of appropriate metabolic enzymes.

Clinical Evaluation of NM324

Figure 10:
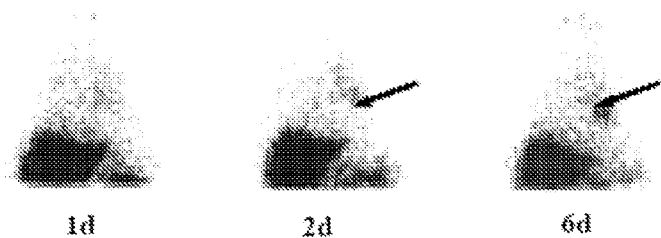
FIG. 10 is a scintigraphic image of the anterior chest of Patient 03 acquired at 1, 2, and 6 days after iv administration of 1 mCi $^{131}$I-NM324. Uptake is seen in the left lingular lung cancer (T) with increasing tumor-to-background ratios over time.

Although first generation compounds NM324 and NM294 displayed similar animal tumor localization characteristics, NM324 was easier to chemically synthesize and was thus selected as the lead compound for initial clinical studies. Although images obtained in several human lung cancer patients detected tumors, images were complicated by high liver radioactivity (FIG. 10).

Second Generation PLE Analogs

In order to decrease liver uptake and prolong the plasma phase, the inventors examined 9 structural analogs of NM324 to identify agents that would display improved tumor-to-background tissue ratios with decreased liver uptake. The new PLE analogs were synthesized and radiolabeled with $^{125}$I for initial image analysis in Copenhagen rats bearing Dunning R3327 prostate tumors. Based upon this initial screen, NM404 not only exhibited much lower liver activity than its predecessor NM324 but also maintained prolonged tumor retention, over 20 days (FIG. 7). NM404 was therefore selected to undergo further imaging and biodistribution analysis in a variety of animal-tumor models.

Tissue Distribution and Kinetics

Consistently, NM404 has been found to be retained in tumor tissue for long and extended periods of time. Tumor concentrations are almost stable for many weeks following administration of NM404, showing slow elimination from cancerous tissue over time. In contrast, NM404 is eliminated from normal tissue within a few days.

Figure 11:
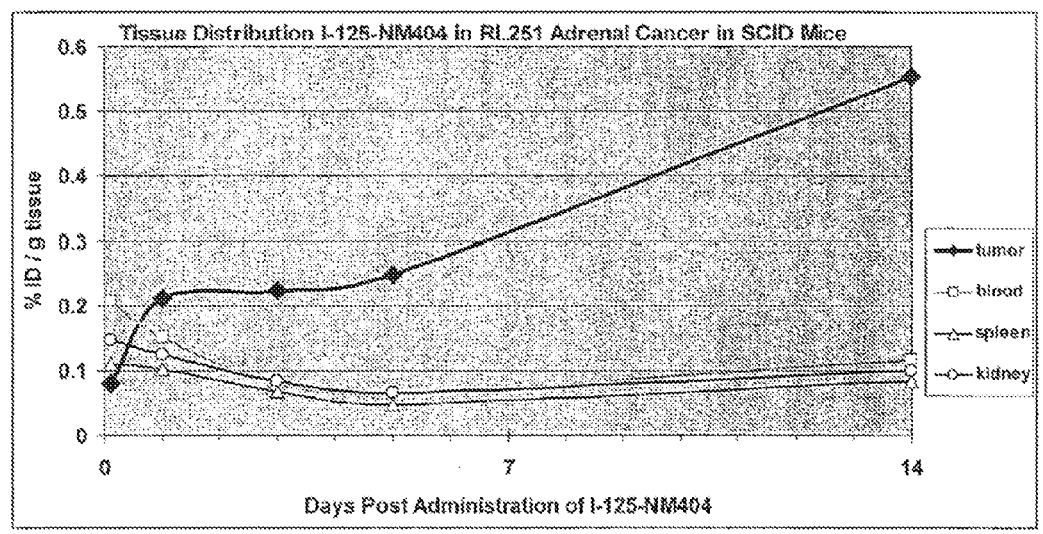
FIG. 11 is a graph illustrating the tissue distribution $^{125}$I-NM404 in RL 251 Adrenal Cancer in SCID mice depicting that while accumulation in the tumor increased, distribution in blood, spleen and kidney reduced by days 1 through 14.
Figure 12:
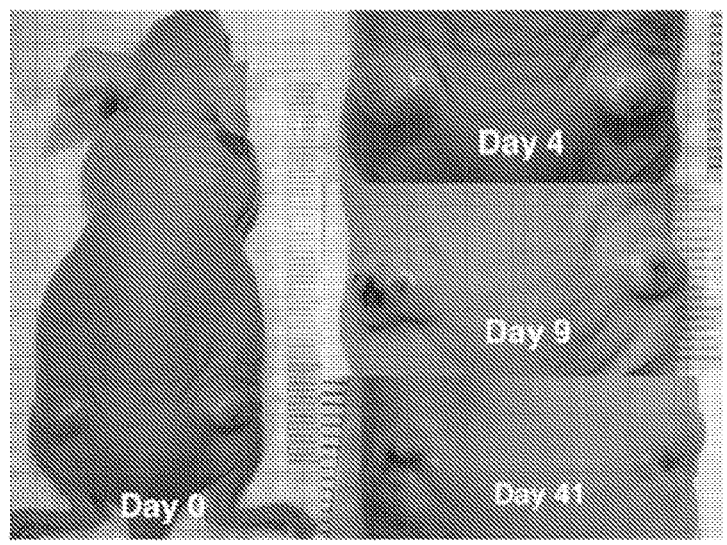
FIG. 12 shows images illustrating the SCC1 and SCC6 tumor regression after injection of $^{125}$I-NM404. By day 41, the tumor is significantly reduced.

Additionally, NM404 was designed to have a long blood half life. This ensures prolonged exposure of NM404 to neoplastic cells and ensures uptake of up to 10-25% of the injected dose into the tumor tissue. The inventors believe that it is very important for a radiotherapy compound to have a large portion of the injected dose accumulating in the tissue of interest. As a consequence of the long blood half life, NM404 will continuously accumulate in tumor tissue over time. An example of this pattern is provided in FIG. 11. This may allow multiple radiotherapy treatments for a single PLE dose due to the ability of PLE's like of NM404 to accumulate in the cancer tissue for several days or weeks.

Blood Plasma Kinetics

The first-generation prototype compound NM324 was found to have a elimination half life time in plasma of 2.43 hours in rats. By comparison, the lead compound NM404, has a elimination half life time of roughly 209 hours in rats (distribution phase half life is 4.86 hours).

Radiotherapeutic Study of $^{125}$I-NM404

During the course of mouse tumor uptake and retention studies with "imaging" doses (15-20 µCi/20 g mouse) of $^{125}$I-labeled NM404, several apparent therapeutic responses have been observed (unpublished results). In an Apc$^{Min}$/+ mouse mammary tumor model it has generally been noted that tumor growth remains static following a single intravenous injection of radioiodinated NM404. Some of these animals also lost all hair above larger mammary tumors at around 8 days after injection. Moreover, these mice also get intestinal tumors and usually suffer from intestinal bleeding resulting in severe anemia, which renders their feet white. It has been noted that the feet of these mice had reverted to a pink color around 5 days after a single injection of NM404. Upon eventual dissection of these animals, it was noted that only a very few, if any, of the expected 20 or so intestinal tumors usually found at this age actually remained. The "white to pink feet" phenomenon was also observed in a separate, but more aggressive, mouse intestinal adenocarcinoma model, wherein dissection at 12 days following NM404 administration, again revealed that most, if not all, of the expected intestinal tumors were gone. After 21 days In both intestinal models, animals that received NM404 easily outlived their untreated litter mates. Another compelling example of tumor regression is illustrated in FIG. 13. Two litter mates each received SCC1 and SCC6 xenografts in their left and right flanks, respectively. One mouse received a single injection of $^{125}$I-NM404 (20 µCi). The mouse that didn't receive NM404 died 21 days later, whereas the tumors in the treated mouse regressed significantly and the animal was quite healthy 80 days after injection. These coincidental findings were reconfirmed in two separate age-matched groups each involving more than 6 mice. Thus, these results indicate that there is a prolonged and specific retention of the PLE analogs directly at the site of the tumor (the affected tissue) and the sequestration of PLE precisely at the cells to be treated by radiotherapy.

Thus, as described above, the inventors have identified that boronic conjugates of phospholipid ether analogs are ideally suited for use in radiation therapy. Further, in some exemplary embodiments the boronic conjugates disclosed are boronic esters of PLE analogs. In addition, as disclosed above, the boronic esters are non-toxic and include the PLE characteristic described herein of being tumor specific and targeting only neoplastic cells. Of course it should be appreciated by those of skill in the art that the boronic conjugates of the PLE analogs disclosed herein can be used alone or in conjunction with other cancer treatments or even, for example, other PLE analogs, such as for example, radiolabeled PLE's such as those described, for example, in U.S. patent application Ser. No. 11/671,403 incorporated herein in its entirety for all purposes.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A boronic acid or ester of a phospholipid ether analog having the structure:

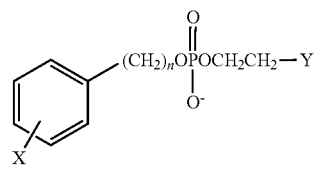

wherein X is selected from the group consisting of
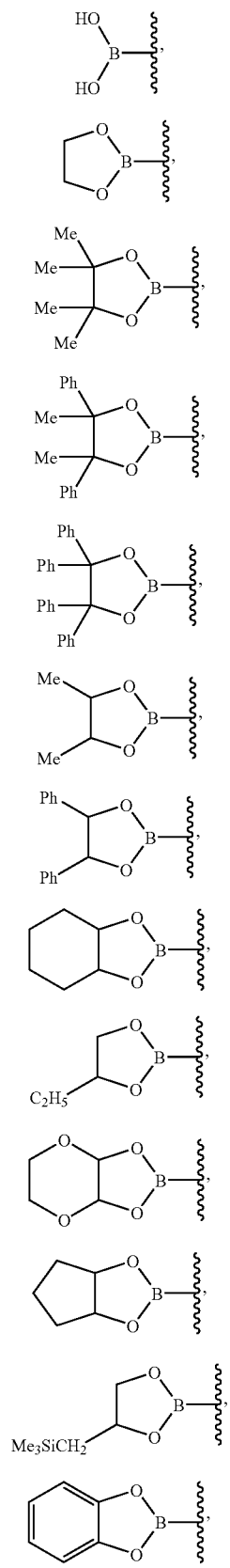
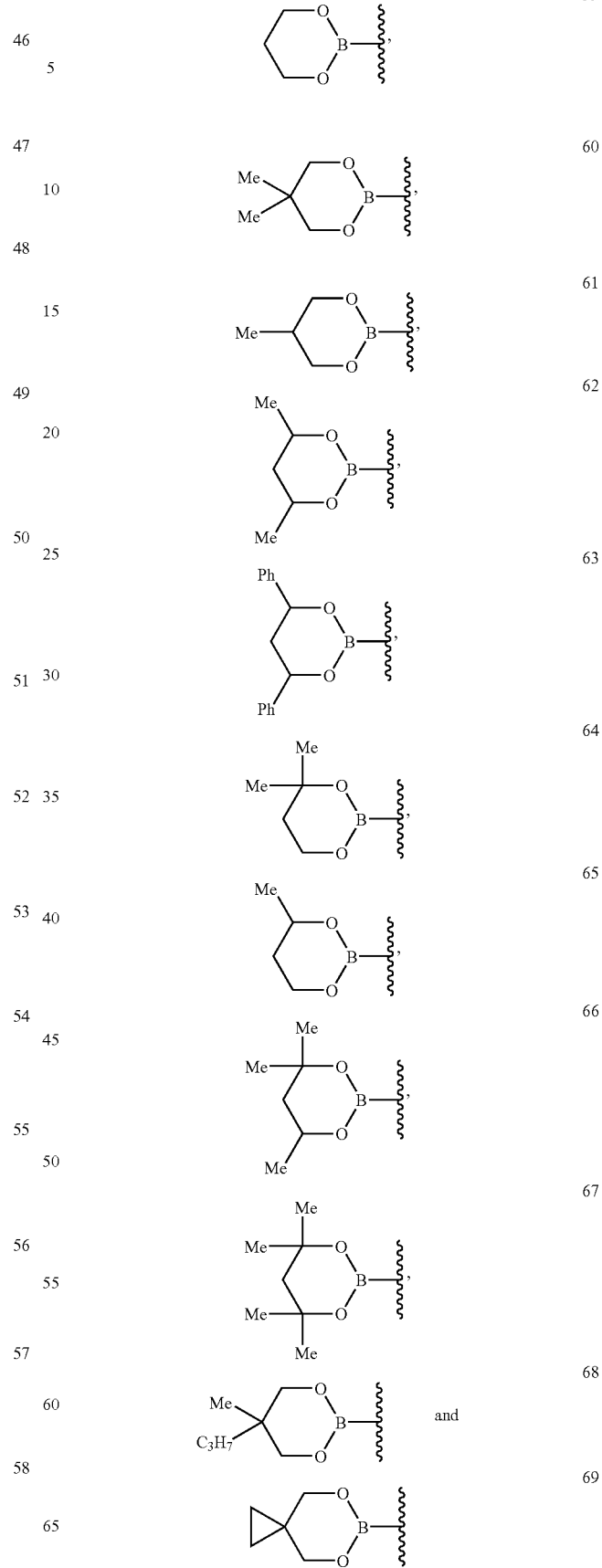

wherein n is an integer between 8 and 30; and Y is selected from the group comprising NH$_2$, NHR, NR$_2$, and NR$_3$, wherein R is an alkyl or arylalkyl substituent.

2. The boronic acid or ester of a phospholipid ether analog of claim 1, wherein the boronic acid or ester of the phospholipid ether analog has the structure:

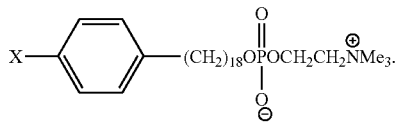

3. A compound having the structure:

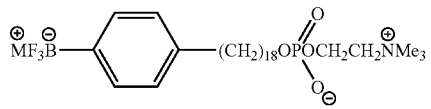

wherein M is selected from the group consisting of Li, Na, K, Cs and Rb and the compound is an intermediate in the synthesis of the boronic ester of the phospholipid ether analog according to claim 2.

4. A boronic ester of a phospholipid ether analog having the structure

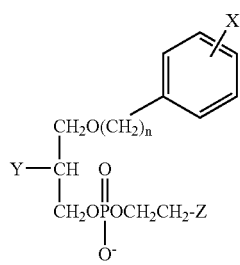

wherein X is selected from the group consisting of

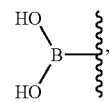 46

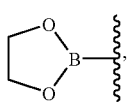 47

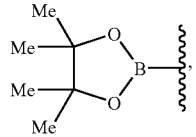 48

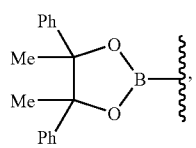 49

-continued

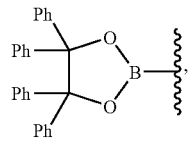 50

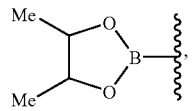 51

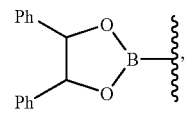 52

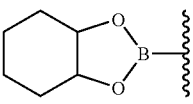 53

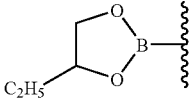 54

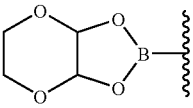 55

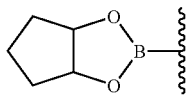 56

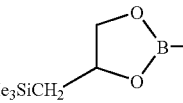 57

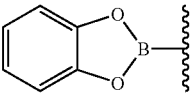 58

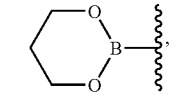 59

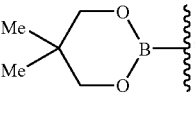 60

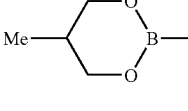 61

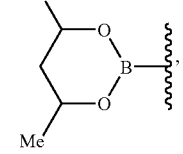 62

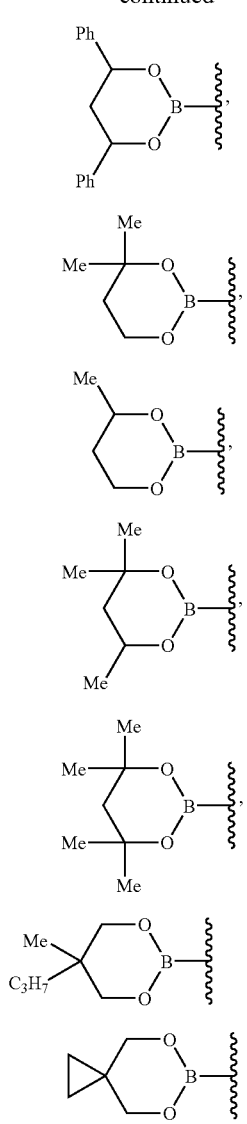

where n is an integer between 8 and 30; and Y is selected from the group consisting of H, OH, OCH₃, OC₂H₅, OC₃H₇; and Z is selected from the group consisting of NH₂, NHR, NR₂ and NR₃, wherein R is an alkyl or arylalkyl substituent.

5. A method of synthesizing a high specific activity phospholipid ether (PLE) analog, comprising the steps of:
  (a) coupling an ester of diboron with a PLE or APC analog in the presence of a catalyst to result in a boronic acid or ester PLE or APC analog;
  (b) esterifying the boronic acid of the PLE analog with 1,2- or 1,3-diols to result in the boronic esters of PLE or APC analog to step (a); and
  (c) reacting the boronic acid or ester of PLE or APC analog of step (a) or (b) with sodium radiohalide, in the presence of an oxidant to result in a high specific activity radiohalogenated PLE or APC analog,
and wherein said specific activity phospholipid ether (PLE) analog is labeled with $^{125}I$ or $^{131}I$.

6. The method of claim 5, wherein the coupling reaction of step (a) is carried out with methanol as a solvent at temperature of about 15-70° C. in the presence of a Pd catalyst.

7. The method of claim 6, wherein in step (c) the oxidant is selected from the group consisting of: dichloramine-T, chloramine-B, dichloramine-B, iodogen, iodogen coated tubes, iodobeads, N-chlorosuccinimide, hydrogen peroxide, peracetic acid, m-chloro-perbenzoic acid and peroxidase.

8. The method of claim 5, wherein the catalyst is

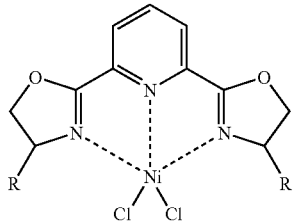

wherein R is selected from the group consisting of: H for Pybox, i-Pr for i-Pr-Pybox, s-Bu for s-Bu-Pybox, and Ph for Ph-Pybox.

9. The method of claim 5, wherein the synthesis of the high specific activity PLE analog proceeds through an intermediate having the structure:

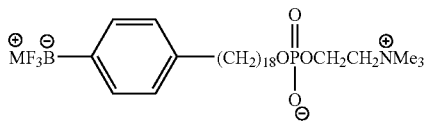

wherein M is selected from the group consisting of Li, Na, K, Cs and Rb and the compound is an intermediate in the synthesis of the boronic ester of the phospholipid ether analog according to claim 3.

10. A method of decreasing the growth of cancer wherein the method comprises:
  (a) administering to a patient in need thereof a boron-conjugated phospholipid ether analog; and
  (b) administering radiation therapy to the patient;
  wherein cancer cells are bombarded by radiation thereby decreasing the growth of cancer.

11. The method according to claim 10, wherein the radiation therapy is external radiation therapy, internal radiation therapy, neutron beam radiation therapy or combinations thereof.

12. The method according to claim 10, wherein the boron-conjugated phospholipid ether analog has the structure:

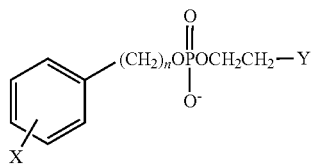

wherein X is selected from the group consisting of:

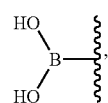

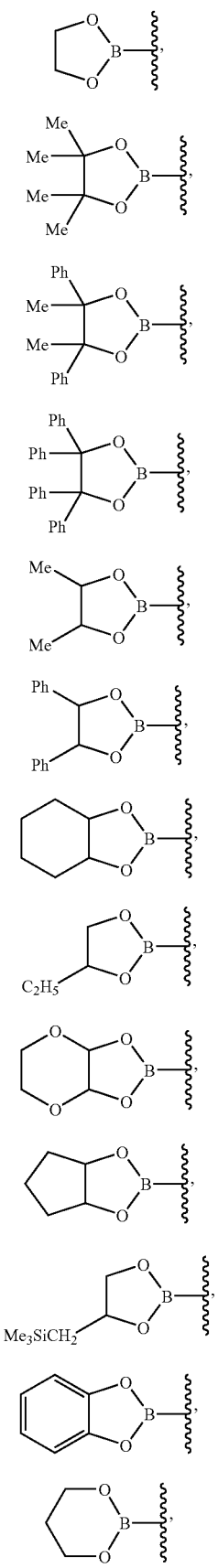
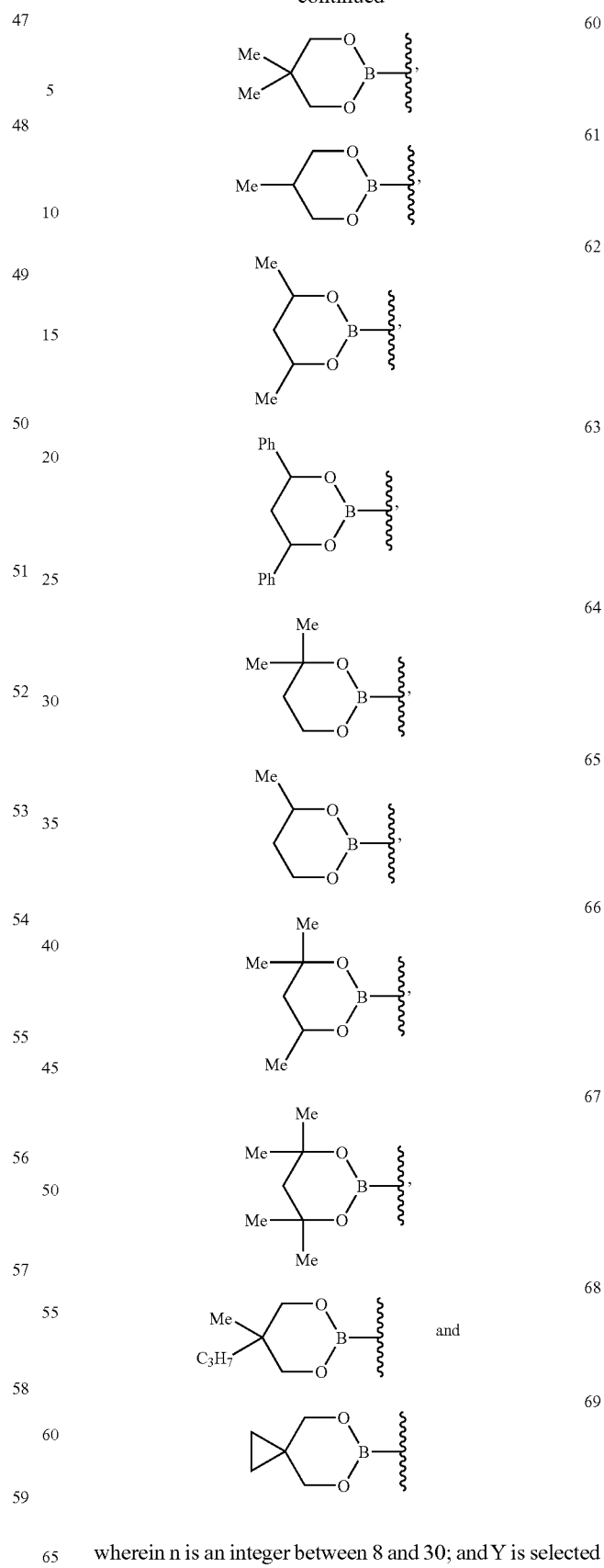
wherein n is an integer between 8 and 30; and Y is selected from the group comprising $NH_2$, NHR, $NR_2$, and $NR_3$, wherein R is a, an alkyl or arylalkyl substituent.

13. The method according to claim 12, wherein the boronic acid or ester of the phospholipid analog has the structure:

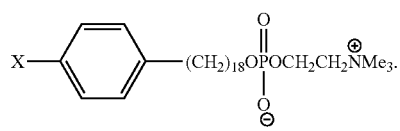

14. The method according to claim 10, wherein the cancer is selected from a group consisting lung cancer, adrenal cancer, melanoma, colon cancer, colorectal cancer, ovarian cancer, prostate cancer, liver cancer, subcutaneous cancer, squamous cell cancer, adenocarcinoma, intestinal cancer, hepatocellular carcinoma, retinoblastoma, cervical cancer, glioma, breast cancer, pancreatic cancer, carcinosarcoma, hepatoma and carcinosarcoma.

* * * * *